United States Patent
Farrugia et al.

(10) Patent No.: US 12,202,788 B2
(45) Date of Patent: Jan. 21, 2025

(54) GRADIENT MEMBRANES FORMED FROM FREE STANDING STRUCTURED ORGANIC FILMS AND METHODS THEREOF

(71) Applicant: XEROX CORPORATION, Norwalk, CT (US)

(72) Inventors: Valerie M. Farrugia, Oakville (CA); Shivanthi Easwari Sriskandha, Mississauga (CA); Matthew A. Heuft, Oakville (CA)

(73) Assignee: XEROX CORPORATION, Norwalk, CT (US)

( * ) Notice: Subject to any disclaimer, the term of this patent is extended or adjusted under 35 U.S.C. 154(b) by 173 days.

(21) Appl. No.: 17/946,001

(22) Filed: Sep. 15, 2022

(65) Prior Publication Data

US 2024/0116858 A1    Apr. 11, 2024

(51) Int. Cl.
*C07C 309/42*    (2006.01)

(52) U.S. Cl.
CPC .................................. *C07C 309/42* (2013.01)

(58) Field of Classification Search
CPC .................................................. C07C 309/42
See application file for complete search history.

(56) References Cited

U.S. PATENT DOCUMENTS

| | | | |
|---|---|---|---|
| 5,119,314 A | 6/1992 | Hotta et al. | |
| 7,108,935 B2 | 9/2006 | Bauer et al. | |
| 8,029,857 B2 | 10/2011 | Hoek et al. | |
| 8,093,347 B2 | 1/2012 | Heuft et al. | |
| 8,119,315 B1 | 2/2012 | Heuft et al. | |
| 8,264,516 B2 | 9/2012 | Steven et al. | |
| 8,313,560 B1 | 11/2012 | Cote et al. | |
| 8,318,892 B2 * | 11/2012 | Cote | C07C 213/06 528/211 |
| 8,353,574 B1 | 1/2013 | Heuft et al. | |
| 8,377,999 B2 | 2/2013 | Cote et al. | |

(Continued)

FOREIGN PATENT DOCUMENTS

| | | |
|---|---|---|
| CN | 107915658 B | 4/2020 |
| EP | 3440239 B1 | 11/2020 |

(Continued)

OTHER PUBLICATIONS

Author Unknown, "Fuel Cells—Alkaline Anion Exchange Membranes," The Department of Chemistry & Chemical Biology, Abruna Electrochemistry, date unknown, 5 pages.

(Continued)

*Primary Examiner* — Maria V Ewald
*Assistant Examiner* — Donald M Flores, Jr.
(74) *Attorney, Agent, or Firm* — MH2 Technology Law Group LLP

(57) ABSTRACT

A structured organic film (SOF) is disclosed. The structured organic film includes a plurality of segments, a plurality of linkers, and a plurality of capping segments. The structured organic film also includes a first surface of the SOF. The film also includes a parallel second surface of the SOF connected to the first surface by a thickness of the SOF, where a segment to capping segment ratio is greater at the first surface as compared to the parallel second surface. A membrane including a free-standing film comprised of a structured organic film is also disclosed.

18 Claims, 6 Drawing Sheets

(56) References Cited

U.S. PATENT DOCUMENTS

| | | | |
|---|---|---|---|
| 8,389,060 B2 | 3/2013 | Heuft et al. | |
| 8,410,016 B2 | 4/2013 | Cote et al. | |
| 8,436,130 B2 | 5/2013 | Cote et al. | |
| 8,518,253 B2 | 8/2013 | Xiong et al. | |
| 8,529,997 B2 | 9/2013 | Heuft et al. | |
| 8,591,997 B2 | 11/2013 | Heuft et al. | |
| 8,765,340 B2 | 7/2014 | Vella et al. | |
| 8,906,462 B2 | 12/2014 | Wigglesworth et al. | |
| 9,097,995 B2 | 8/2015 | Heuft et al. | |
| 9,309,343 B2 | 4/2016 | Van Berchum et al. | |
| 9,375,678 B2 | 6/2016 | Nair et al. | |
| 9,580,824 B2 | 2/2017 | Masel et al. | |
| 9,768,502 B2 | 9/2017 | Lin | |
| 9,815,032 B2 | 11/2017 | Hill et al. | |
| 9,950,549 B2 | 4/2018 | Kanungo et al. | |
| 10,076,728 B2 | 9/2018 | Song et al. | |
| 10,258,932 B2 | 4/2019 | Birss et al. | |
| 10,281,831 B2 | 5/2019 | Cote et al. | |
| 10,347,939 B2 | 7/2019 | Choi et al. | |
| 10,384,441 B2 | 8/2019 | Badesha et al. | |
| 10,570,524 B2 | 2/2020 | Matthews et al. | |
| 10,710,065 B2 | 7/2020 | Helms et al. | |
| 10,792,392 B2* | 10/2020 | Kourtis | A61L 27/18 |
| 10,869,950 B2 | 12/2020 | Kourtis et al. | |
| 2007/0055045 A1 | 3/2007 | Kiefer et al. | |
| 2010/0224867 A1* | 9/2010 | Heuft | C09B 26/02 |
| | | | 544/71 |
| 2011/0217642 A1 | 9/2011 | Heuft et al. | |
| 2011/0281197 A1 | 11/2011 | Daikoku | |
| 2014/0099571 A1 | 4/2014 | Proietti et al. | |
| 2017/0240473 A1 | 8/2017 | Budarin et al. | |
| 2019/0074710 A1 | 3/2019 | Hansen | |
| 2019/0168173 A1 | 6/2019 | Tsapatsis et al. | |
| 2019/0322114 A1 | 10/2019 | Sambhy et al. | |
| 2020/0388871 A1 | 12/2020 | Newbloom et al. | |
| 2021/0047242 A1 | 2/2021 | Liu et al. | |

FOREIGN PATENT DOCUMENTS

| | | |
|---|---|---|
| WO | WO 2006/016068 A2 | 2/2006 |
| WO | 2012045152 A1 | 4/2012 |
| WO | WO 2018/193021 A1 | 10/2018 |
| WO | 2022144900 A1 | 7/2022 |

OTHER PUBLICATIONS

Agari et al., "Estimation of the compositional gradient in a PVC/PMMA graded blend prepared by the dissolutionediffusion method," ScienceDirect, Polymer (2007) 1139-1147.

Alabi et al., "Electrostatically-coupled graphene oxide nanocomposite cation exchange membrane," Journal of Membrane Science 594 (2020) 117457, 10 pages.

Banerjee et al., "Nafion Perfluorinated Membranes in Fuel Cells," Journal of Fluorine Chemistry 125 (2004) 1211-1216, 6 pages.

Cho et al., "Engineering Synergy: Energy and Mass Transport in Hybrid Nanomaterials," Advanced Materials 2015, 27, 5744-5752.

Chu et al., "Practical Implementation of bis-six-membered N-cyclic Quaternary Ammonium Cations in Advanced Anion Exchange Membranes for Fuel Cells: Synthesis and Durability," Journal of Membrane Science 578 (2019) 239-250.

Claussen et al., "Longitudinal polymer gradient materials based on crosslinked polymers," Polymer 55 (2014) 29-38.

Henkensmeier et al., "Overview: State-of-the Art Commercial Membranes for Anion Exchange Membrane Water Electrolysis," Journal of Electrochemical Energy Conversion and Storage, May 2021, vol. 18, pp. 024001-1 through 024001-18.

Holloczki et al., "Hydrolysis of Imidazole-2-ylidenes," Journal of the American Chemical Society, 2011, 133, 780-789.

Inagi, "Fabrication of Gradient Polymer Surfaces Using Bipolar Electrochemistry," Polymer Journal (2016) 48, 39-44.

Jaroszek et al., "Ion-exchange Membranes in Chemical Synthesis a Review," Open Chem. (2015) 14, 1-19.

Kaczur et al., "Carbon Dioxide and Water Electrolysis Using New Alkaline Stable Anion Membranes," Frontiers in Chemistry Technology Report, Jul. 2018, vol. 6, article 263, 16 pages.

Kaczur et al., "A Review of the Use of Immobilized Ionic Liquids in the Electrochemical Conversion of $CO_2$," Journal of Carbon Research (2020) 6, 33, 12 pages.

Kandambeth et al., "Selective Molecular Sieving in Self-Standing Porous Covalent-Organic-Framework Membranes," Advanced Materials 2017, 29, 1603945.

Kayser et al., "Cross-linked Sulfonated Poly(ether ether ketone) by Using Diamino-organosilicon for Proton Exchange Fuel Cells," The Journal of Physical Chemistry B (2011) 115, 2916-2923.

Koshikawa et al., "Single Nanometer-Sized NiFe-Layered Double Hydroxides as Anode Catalyst in Anion Exchange Membrane Water Electrolysis Cell with Energy Conversion Efficiency of 74.7% at 1.0 A $cm^{-2}$," American Chemical Society, ACS Catal. (2020) 10, 1886-1893.

Lee et al., "Poly(terphenylene) Anion Exchange Membranes: The Effect of Backbone Structure on Morphology and Membrane Property," ACS Macro Letters (2017) 6, 566-570.

Li et al., "Recent advances in the fabrication of advanced composite membranes," J. Mater. Chem. A, Jan. 2013, 10058-10077.

Lin et al., Two-dimensional covalent triazine framework as an ultrathin-film nanoporous membrane for Desalination, Chem. Commun., 2015, 51, 14921-14924.

Liu et al., "Functional gradients and heterogeneities in biological materials: Design principles, functions, and bioinspired applications," Progress in Materials Science (2017), 88, 467-498.

Lu et al., "A novel 3D covalent organic framework membrane grown on a porous $\alpha$-$Al_2O_3$ substrate under solvothermal conditions," Chem. Commun., 2015, 51, 15562-15565.

Meng et al., "2D and 3D Porphyrinic Covalent Organic Frameworks: The Influence of Dimensionality on Functionality," Angew. Chem. 2020, 132, 3653-3658.

Meyers et al., "Structural Biological Materials: Critical Mechanics-Materials Connections," Science, vol. 339, Feb. 15, 2013, 773-779.

Moon et al., Sufonated PEEK Ion Exchange Membranes for Direct Methanol Fuel Cell Applications, Macromolecular Research (2007) vol. 15, No. 4, pp. 379-384.

Oh et al., "In vitro and in vivo characteristics of PCL scaffolds with pore size gradient fabricated by a centrifugation method," Biomaterials 28 (2007), 1664-1671.

Pedron et al, "Microfluidic approaches for the fabrication of gradient crosslinked networks based on poly(ethylene glycol) and hyperbranched polymers for manipulation of cell interactions," Journal of Biomedical Materials Research A, Jan. 2011, vol. 96, Issue 1, 196-203.

Qiu et al., "Alkaline imidazolium- and quaternary ammonium-functionalized anion exchange membranes for alkaline fuel cell applications," J. Mater. Chem., 2012, 22, 1040.

Ran et al., "Ion exchange membranes: New developments and applications," Journal of Membrane Science 522 (2017) 267-291.

Suhaimin et al., "Methanol Permeability and Properties of Polymer Electrolyte Membrane Based on Graphene Oxidesulfonated (Polyether Ether) Ketone)," Malaysian Journal of Analytical Sciences, vol. 21, No. 2 (2017), 435-444.

Teng et al., "Preparation of Compositional Gradient Polymeric Films Based on Gradient Mesh Template," Polymers (2018) 10, 677 (15 pages).

Author Unknown, "Polymer(matrix) structure—A236," CKN Knowledge in Practice Centre, date unknown, 7 pages.

Varcoe et al., "Anion-exchange membranes in electrochemical energy systems," Energy Environ. Sci., Jul. 2014, 3135-3191.

Wang et al., "Efficient electrically powered $CO_2$-to-ethanol via suppression of deoxygenation," Nature Energy, 2020, 9 pages.

Wang et al., "N-cyclic quaternary ammonium-functionalized anion exchange membrane with improved alkaline stability enabled by aryl-ether free polymer backbones for alkaline fuel cells," Journal of Membrane Science 587, (2019), 117135.

Wang et al., "Novel Hydroxide-Conducting Polyelectrolyte Composed of an Poly(arylene ether sulfone) Containing Pendant Quaternary Guanidinium Groups for Alkaline Fuel Cell Applications," Macromolecules 2010, 43, 3890-3896.

(56) References Cited

OTHER PUBLICATIONS

Wang et al., "Stabilizing the Imidazolium Cation in Hydroxide-Exchange Membranes for Fuel Cells," ChemSusChem Jun. 2013, 2079-2082.
Yang et al., "Functionally graded membranes from nanoporous covalent organic frameworks for highly selective water permeation," Journal of Materials Chemistry A, Jun. 2018, 583-591.
Yang et al., The Application of Cation Exchange Membranes in Electrochemical Systems for Ammonia Recovery from Wastewater, Membranes Nov. 2021, 494 (14 pages).
Yee et al., "The Effects of Sulfonated Poly(ether ether ketone) Ion Exchange Preparation Conditions on Membrane Properties," Membranes Mar. 2013, 182-195.
Zhang et al., "Novel cross-linked anion exchange membranes with diamines as ionic exchange functional groups and crosslinking groups," International Journal of Hydrogen Energy 39 (2014) 13718-13724.
Extended European Search Report mailed in EP 23193650.1 on Feb. 19, 2024. (9 pages).
Aggarwal et al., "Ligand Valency Effects on the Alkaline Stability of Metallopolymer Anion-Exchange Membranes," Macromolecular Rapid Communications, vol. 42, Article 2100238, 2021 (Published online Jun. 25, 2021), 6 pages.
Disabb-Miller et al., "Water Uptake and Ion Mobility in Cross-Linked Bis(terpyridine)ruthenium-Based Anion Exchange Membranes," Macromolecules, vol. 46, 2013 (Published Nov. 22, 2013), pp. 9279-9287.
Kwasny et al., "Expanding metal cation options in polymeric anion exchange membranes," Journal of Materials Chemistry A, vol. 5, 2017 (Published Dec. 5, 2016), pp. 1400-1405.
Leech et al., "Effect of Composition of Polymer Backbone on Spectroscopic and Electrochemical Properties of Ruthenium(II) Bis(2,2'-bipyridyl)-containing 4-Vinylpyridine/Styrene Copolymers," Journal of Materials Chemistry, vol. 1, No. 4, Jan. 1991, pp. 629-635 (8 pages).
Yuan et al., "Ring-opening metathesis polymerization of cobaltocenium derivative to prepare anion exchange membrane with high ionic conductivity," Polyhedron, vol. 181, Article 114462, 2020 (Available online Mar. 2, 2020), pp. 1-7.
Zha et al., "Metal-Cation-Based Anion Exchange Membranes," Journal of the American Chemical Society (JACS), vol. 134, 2012 (Published Mar. 2, 2012), pp. 4493-4496.
Zhu et al., "Cationic Metallo-Polyelectrolytes for Robust Alkaline Anion-Exchange Membranes," Author Manuscript, Angew. Chem. Int. Ed., vol. 57, No. 9, Feb. 23, 2018 (First published Dec. 31, 2017), pp. 2388-2392 (7 pages).
Zhu et al., "Rational Synthesis of Metallo-Cations Toward Redox- and Alkaline-Stable Metallo-Polyelectrolytes," Journal of the American Chemical Society (JACS), vol. 142, 2020 (Published Dec. 17, 2019), pp. 1083-1089.
Extended European Search Report mailed in EP 23196462.8 on Mar. 12, 2024. (8 Pages).
Extended European Search Report for European Application No. 23193647.7 dated Feb. 5, 2024, 9 pages.
Extended European Search Report for European Application No. 23193651.9 dated Feb. 2, 2024, 18 pages.
Claridge, Robert, "Physically Reinforced Structured Organic Film (SOF) Anion Exchange Membranes (AEMs)," U.S. Appl. No. 18/229,427, filed Aug. 2, 2023, 49 pages.
Marino, M.G., et al., "Alkaline Stability of Quaternary Ammonium Cations for Alkaline Fuel Cell Membranes and Ionic Liquids," ChemSusChem., vol. 8, 2015 (Published online Nov. 27, 2014), pp. 513-523.
Min, K., et al., "Crosslinked poly(m-terphenyl N-methyl piperidinium)—SEBS membranes with aryl-ether free and kinked backbones as highly stable and conductive anion exchange membranes," Journal of Membrane Science, vol. 653, Article 120487, 2022 (Available online Mar. 21, 2022), 11 pages.
Yuan, Y., et al., "Preparation of an Anion Exchange Membrane by Pyridine-Functionalized Polyether Ether Ketone To Improve Alkali Resistance Stability for an Alkali Fuel Cell," Energy Fuels, vol. 35, No. 4, Feb. 1, 2021, pp. 3360-3367.
Farrugia, V.M., et al., "Cation Exchange Membranes From Structured Organic Films and Methods Thereof," U.S. Appl. No. 17/946,003, filed Sep. 15, 2022, 39 pages.
Farrugia, V.M., et al., "Anion Exchange Membranes From Structured Organic Films and Methods Thereof," U.S. Appl. No. 17/946,006, filed Sep. 15, 2022, 38 pages.
Claridge, R., et al., "Structured Organic Films Containing Imidazolium Having Cationic Charge Functionality and Methods Thereof," U.S. Appl. No. 17/946,007, filed Sep. 15, 2022, 38 pages.
Claridge, R., et al., "Structured Organic Films Containing N-Cyclic Quaternary Ammonium Having Cationic Charge Functionality and Methods Thereof," U.S. Appl. No. 18/051,800, filed Nov. 1, 2022, 42 pages.
Morimitsu, K., et al., "Ion Exchange Membranes (IEMS) With Ionic Ligand-Metal Complexes and Methods Thereof," U.S. Appl. No. 18/169,098, filed Feb. 14, 2023, 17 pages.
Farrugia, V., et al., "Flexible Structured Organic Film Membrane Formulations and Methods Thereof," U.S. Appl. No. 18/218,420, filed Jul. 5, 2023, 43 pages.
Claridge, R., et al., "Flexible Ionic Building Blocks With High Ionic Conductivity and Alkaline Stability for Use in Structured Organic Film (SOF) Containing Anion Exchange Membranes (AEMs)," U.S. Appl. No. 18/218,445, filed Jul. 5, 2023, 45 pages.

\* cited by examiner

GRADIENT MEMBRANES FORMED FROM FREE STANDING STRUCTURED ORGANIC FILMS AND METHODS THEREOF

TECHNICAL FIELD

The present teachings relate generally to free-standing structured organic films and, more particularly, to gradient membrane compositions formed from free-standing structured organic films.

BACKGROUND

Self-standing membranes fabricated from covalent organic frameworks (COFs) and structured organic frameworks (SOFs) shown to have ordered pore channels and low mass transfer resistance resulting in excellent separation performance have been studied. Other approaches use a hybrid approach where COFs are homogeneously dispersed into polymeric matrices but result in voids and COF pore blockage by the polymer component. Some other methods that have been used to prepare gradient films include dissolution and diffusion methods, extrusion, microfluidic techniques, electrochemical techniques and centrifugation.

Traditional membranes can be based on polymeric materials which contain pores formed by the entanglement and flexible nature of the polymer chains. These membranes are designed at the molecular-level from hydrophobic polymers such as polyvinylidene fluoride (PVDF). The fabrication of these nanofiber membranes are produced by electrospinning and are not easily manipulated into gradient films or films exhibiting a porosity gradient across a thickness of a membrane.

Additional methods for fabrication of porous gradient films include salt-leaching, cryogel technology where pore materials are created by a freeze-drying, cryogenic treatment that includes the removal of ice crystals and temperature gradients during the freezing step that results in scaffold-like pores. In another example, gradient films can be prepared by incorporating polydimethylsiloxane (PDMS) components into a gradient gelatin mesh template, with the distribution of PDMS gradually changing along the thickness of the film. Colloidal particles of mono-epoxy terminated polydimethylsiloxane (PDMS-E) grafted gelatin (PGG) of suitable size are then used to fill the gradient mesh template resulting in a decrease of average porosity from 35 to 89% and pore sizes ranging from 50 to 160 microns.

Issues with the currently known methods of fabricating functionally graded materials include sensitivity to a variety of factors such as solvent, concentration of reagents, pH, temperature and additives such as leveling agents or surfactant that may interfere with both covalent and non-covalent interactions among the reactants. Other complications include a lack of compatibility or dissolution of the reagents in polar or non-polar systems.

Therefore, it is desirable to fabricate functionally graded materials or gradient films synthesized from ordered network systems to be used in a variety of applications such as gas absorption, energy storage and catalysis.

SUMMARY

The following presents a simplified summary in order to provide a basic understanding of some aspects of one or more embodiments of the present teachings. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later.

A structured organic film (SOF) is disclosed. The structured organic film includes a plurality of segments, a plurality of linkers, and a plurality of capping segments. The structured organic film also includes a first surface of the SOF. The film also includes a parallel second surface of the SOF connected to the first surface by a thickness of the SOF, where a segment to capping segment ratio is greater at the first surface as compared to the parallel second surface.

Implementations of the structured organic film may include where all of the plurality of linkers are bonded to the plurality of segments. At least one of the plurality of capping segments is connected through linkers to at least one of the plurality of segments. A concentration of ionic capping segments in the SOF is from about 0.1 to about 5.0 molar equivalents of ionic capping segments as compared to a concentration of nonionic segments in the SOF. A thickness of the SOF is from about 100 nm to about 500 μm. At least one of the plurality of capping segments may include an acid-functional group. At least one of the plurality of capping segments may include a sulfonic acid. At least one of the plurality of capping segments may include 4-hydroxybenzene sulfonic acid (4HBenSA). At least one of the plurality of capping segments may include 4-hydroxybenzoic acid. At least one of the plurality of capping segments may include hydroxybenzene.

A membrane including a free standing film may include a first surface and a second surface, and may include a plurality of segments, a plurality of linkers, and a plurality of capping segments. Implementations of the membrane may include where a segment to capping segment ratio is greater at the first surface as compared to the second surface. A segment to capping segment ratio can be smaller at the first surface as compared to the second surface. At least one of the plurality of capping segments may include a sulfonic acid. At least one of the plurality of capping segments may include 4-hydroxybenzene sulfonic acid (4HBensA). A concentration of ionic capping segments in the membrane is from about 0.1 to about 5.0 molar equivalents of ionic capping segments as compared to a total concentration of nonionic segments in the membrane. A free-standing film thickness can be from about 100 nm to about 500 μm.

A structured organic film (SOF) membrane. The structured organic film also includes a plurality of segments and a plurality of linkers. The structured organic film also includes a plurality of capping segments. The structured organic film also includes a first surface of the SOF. The structured organic film also includes a second surface of the SOF, where the film includes a segment to capping segment ratio that is greater at the first surface as compared to the second surface. The film also includes a concentration of ionic capping segments in the SOF is from about 0.1 to about 5.0 molar equivalents of ionic capping segments as compared to a total concentration of nonionic segments in the SOF.

The features, functions, and advantages that have been discussed can be achieved independently in various implementations or can be combined in yet other implementations further details of which can be seen with reference to the following description.

BRIEF DESCRIPTION OF THE DRAWINGS

The accompanying drawings, which are incorporated in and constitute a part of this specification, illustrate embodiments of the present teachings and together with the description, serve to explain the principles of the disclosure. In the figures.

Figure 1:
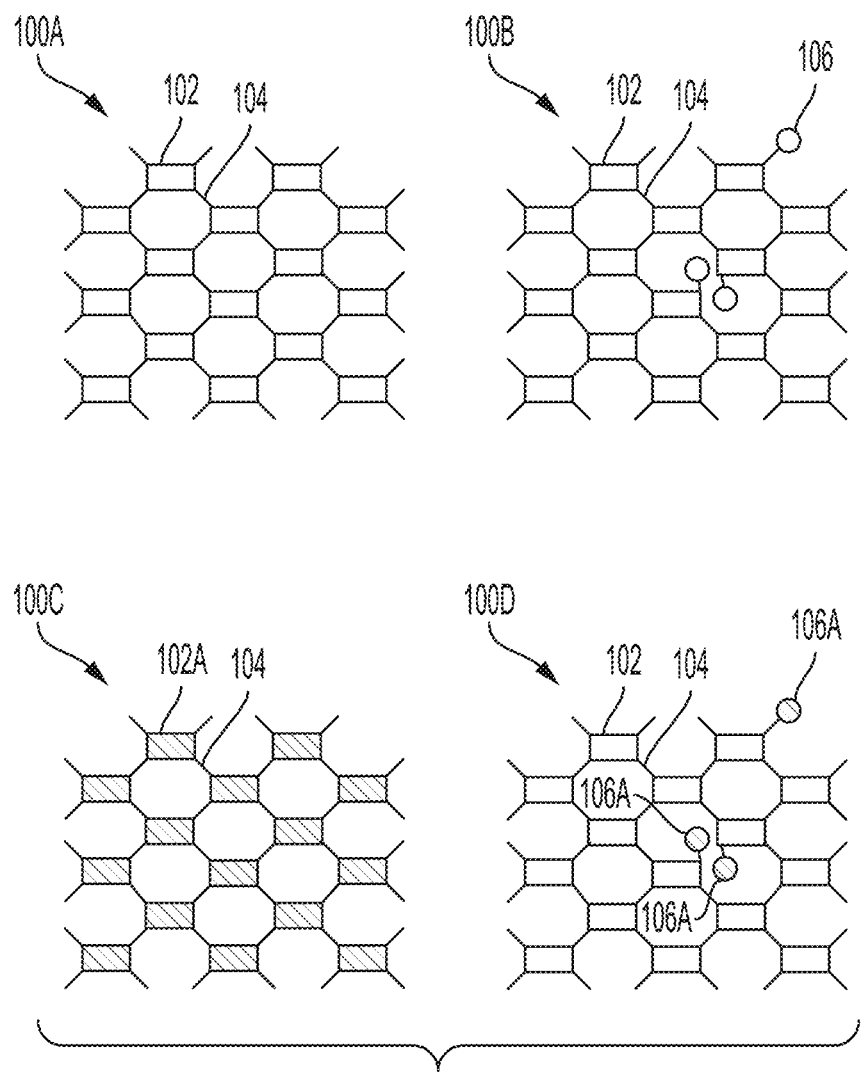
FIG. 1 illustrates the differences between a standard structured organic film, a structured organic film having a capping segment, a structured organic film having molecular building block segments with ionic functionality, and a structured organic film having a capping segment with ionic functionality, in accordance with the present disclosure.

It should be noted that some details of the figures have been simplified and are drawn to facilitate understanding of the present teachings rather than to maintain strict structural accuracy, detail, and scale.

DETAILED DESCRIPTION

Reference will now be made in detail to exemplary embodiments of the present teachings, examples of which are illustrated in the accompanying drawings. Wherever possible, the same reference numbers will be used throughout the drawings to refer to the same, similar, or like parts.

"Structured organic film" (SOF) refers to a COF that is a film at a macroscopic level. The SOFs of the present disclosure have a capping segment or capping group added into the SOF formulation, which (after film formation), ultimately bonds to the SOF via at least one functional group located on the capping segment. SOFs of the present disclosure in certain examples can have non-ionic or ionic character, including cationic or anionic. This ionic character can be imparted by either a charged molecular building block or a capping group in the SOF structure.

In this specification and the claims that follow, singular forms such as "a," "an," and "the" include plural forms unless the content clearly dictates otherwise.

The term "SOF" generally refers to a covalent organic framework (COF) that is a film at a macroscopic level. The phrase "macroscopic level" refers, for example, to the naked eye view of the present SOFs. Although COFs are a network at the "microscopic level" or "molecular level" (requiring use of powerful magnifying equipment or as assessed using scattering methods), the present SOF is fundamentally different at the "macroscopic level" because the film is for instance orders of magnitude larger in coverage than a microscopic level COF network. SOFs described herein have macroscopic morphologies much different than typical COFs previously synthesized. Films as presently disclosed in a free-standing film example, or as coated onto a surface, include but are not limited to, a top surface and a bottom surface, in which "top" and "bottom" can be dependent on a temporal orientation or position of the film. Furthermore, a surface is still considered a surface even if adhered or bound to a substrate or other material. Films as presently disclosed in a free-standing film example, or as coated onto a surface, also include one or more edges, which can be, but are not limited to, one or more boundaries between where a film is present and where a film is not present.

Additionally, when a capping segment is introduced into the SOF, the SOF framework is locally 'interrupted' where the capping segments are present. These SOF compositions are 'covalently doped' because a foreign molecule is bonded to the SOF framework when capping segments are present. Capped SOF compositions may alter the properties of SOFs without changing constituent building block segments. For example, the mechanical and physical properties of the capped SOF where the SOF framework is interrupted may differ from that of an uncapped SOF or an SOF without capping segments.

The SOFs of the present disclosure are at the macroscopic level substantially pinhole-free SOFs or pinhole-free SOFs having continuous covalent organic frameworks that can extend over larger length scales such as for instance much greater than a millimeter to lengths such as a meter and, in theory, as much as hundreds of meters. It will also be appreciated that SOFs tend to have large aspect ratios where typically two dimensions of a SOF will be much larger than the third. SOFs have markedly fewer macroscopic edges and disconnected external surfaces than a collection of COF particles.

In examples, a "substantially pinhole-free SOF" or "pinhole-free SOF" may be formed from a reaction mixture deposited on the surface of an underlying substrate. The term "substantially pinhole-free SOF" refers, for example, to an SOF that may or may not be removed from the underlying substrate on which it was formed and contains substantially no irregular pinholes, blisters, ruptures, or gaps, such as those that would be considered coating defects that could form such as when a bubble ruptures during a film formation that is greater than the distance between the cores of two adjacent segments per square cm; such as, for example, less than 10 pinholes, pores or gaps greater than about 250 nanometers in diameter per $cm^2$, or less than 5 pinholes, pores or gaps greater than about 100 nanometers in diameter per $cm^2$. The term "pinhole-free SOF" refers, for example, to an SOF that may or may not be removed from the underlying substrate on which it was formed and contains no unintended pinholes or gaps greater than the distance between the cores of two adjacent segments per $micron^2$, such as no pinholes or gaps greater than about 500 Angstroms in diameter per $micron^2$. Pores that are intentionally and uniformly introduced into SOFs as tunable features for transport via a membrane are distinguished from pinholes for the purposes of this disclosure.

Structured organic frameworks or SOFs synthesized according to the present disclosure include functionally graded materials. SOFs fabricated by reticular synthesis of organic compositions in the form of films or coatings feature high quality, free-standing films with tunable thickness exhibiting controlled mesoporosity that varies gradually from porous voids to a dense surface film. These SOF materials exhibit spatially varied compositions based on formulations which include sulfonic acid functionality in certain examples. Examples having sulfonic acid functionality can include functionalized sulfonic acids or sulfonic acid derivatives having a functionality that can participate in the linking chemistry of SOF networks as described herein. Additional functional groups in a sulfonic acid, functionalized sulfonic acid, or sulfonic acid derivative can include, but are not limited to hydroxy functional groups. The concentration gradient of building blocks within the SOF network can transition from ionically charged building blocks to non-ionically charged building blocks or nonionic building block segments. The charge density varies along the films depth as shown and described later in regard to FIG. 2. Examples of the present disclosure exploit this concentration gradient, and thus the properties of the SOF films can be tailored to enhance characteristics such as wettability, charge transport, mechanical, optical and thermal properties as well as the density of key functional groups. Similar to biomaterials from nature such as seashells, bones and teeth, SOF materials of the present disclosure can self-assemble into gradients due to their chemical composition.

Traditional methods for determining the porosity of solid materials include pycnometry and gas adsorption. When measuring the open porosity, the volume of the pores which are accessible to liquid or gas is quantified. Thin films can be difficult to accurately assess due to the very small mass deposition. The primary analytical techniques for porosity determination of thin porous film can include gas sorption, electron microscopy, and ellipsometry. Other techniques known in the art include Rutherford backscattering spectrometry, X-ray methods, for example, X-ray reflectometry, X-ray absorption and X-ray fluorescence, and neutron reflectometry. Some common characteristics for porous solids are specific surface area (SSA), average pore size, and pore-size distribution. The measurable pore-size range using gas sorption measurements depends on the size of the gas molecule employed as the probe and the capability of the equipment to achieve high relative pressures. In the case of nitrogen, the smallest detectable pore size is about 0.4 nm and the largest is approximately 300 nm. For this disclosure the quantifiable range can be from about 0.1 nm to about 2500 nm for aggregated COFs below the SOF film, as visually quantified by SEM cross-sectional images. Microscopy provides a reliable method for analysis of pore geometry and sizes in the mesopore range or above via direct observations of thin cross-sections of solid materials. Depending on the specific pore-size resolution required, optical or electron microscopy can be used. Liquid intrusion by a nonwetting liquid can be used as an acceptable method to measure porosity of films of the present disclosure, as the pores obtained by compositions and methods as described herein range between meso and macropore scales of about 4 nm to about 60 microns, or from about 4 nm to about 2.5 microns.

In embodiments, the SOF comprises at least one atom of an element that is not carbon, such at least one atom selected from the group consisting of hydrogen, oxygen, nitrogen, silicon, phosphorous, selenium, fluorine, boron, and sulfur. In further embodiments, the SOF is a boroxine-, borazine-, borosilicate-, and boronate ester-free SOF.

Molecular Building Block

The SOFs of the present disclosure comprise molecular building blocks also referred to as building block segments having a segment (S) and functional groups (Fg). Molecular building blocks require at least two functional groups (x≥2) and may comprise a single type or two or more types of functional groups. Functional groups are the reactive chemical moieties of molecular building blocks that participate in a chemical reaction to link together segments during the SOF forming process. A segment is the portion of the molecular building block that supports functional groups and comprises atoms that are not associated with functional groups. Further, the composition of a molecular building block segment remains unchanged after SOF formation.

Functional Group

Functional groups are the reactive chemical moieties of molecular building blocks that may participate in a chemical reaction to link together segments during the SOF forming process. Functional groups may be composed of a single atom, or functional groups may be composed of more than one atom. The atomic compositions of functional groups are those compositions normally associated with reactive moieties in chemical compounds. Non-limiting examples of functional groups include halogens, alcohols, ethers, ketones, carboxylic acids, esters, carbonates, amines, amides, imines, ureas, aldehydes, isocyanates, tosylates, alkenes, alkynes and the like. Illustrative examples can also include, but are not limited to haloformyls, oxygen containing groups (e.g. hydroxyls, anhydrides, carbonyls, carboxyls, carbonates, carboxylates, aldehydes, esters, hydroperoxy, peroxy, ethers, and orthoesters), nitrogen-containing groups (e.g. carboxamides, amines, imines, imides, azides, azos, cyanates, isocyanates, nitrates, nitriles, isonitriles, nitrosos, nitros, nitrosooxy), sulfur-containing groups (sulfhydryls, sulfides, disulfides, sulfinyls, sulfos, thiocyanates, isothiocyanates, and carbonothioyls), phosphorous-containing groups (e.g. phosphinos, phosphonos, and phosphates), silicon-containing groups (Si(OH)3, Si(SH)4, silanes, silyls, and siloxanes), boron containing groups (e.g. boronic acid, boronic esters, and boronic ethers), metal or metalloid-containing groups (e.g. Ge(OH)$_3$, Ge(SH)$_4$, AsO$_3$H, AsO$_4$H, As(SH)$_3$, Sn(OH)$_3$, Sn(CH$_3$)$_3$, and Sn(Bu)$_3$).

Molecular building blocks contain a plurality of chemical moieties, but only a subset of these chemical moieties are intended to be functional groups during the SOF forming process. Whether or not a chemical moiety is considered a functional group depends on the reaction conditions selected for the SOF forming process. Functional groups (Fg) denote a chemical moiety that is a reactive moiety, that is, a functional group during the SOF forming process.

In the SOF forming process the composition of a functional group will be altered through the loss of atoms, the gain of atoms, or both the loss and the gain of atoms; or, the functional group may be lost altogether. In the SOF, atoms previously associated with functional groups become associated with linker groups, which are the chemical moieties that join together segments. Functional groups have characteristic chemistries and those of ordinary skill in the art can generally recognize in the present molecular building blocks the atom(s) that constitute functional group(s). It should be noted that an atom or grouping of atoms that are identified as part of the molecular building block functional group may be preserved in the linker group of the SOF. Linker groups are described below.

Capping Segments, Ionic Capping Segments and Ionic Building Blocks

Capping segments of the present disclosure are chemical moieties that 'interrupt' the regular network of covalently bonded segments normally present in an SOF, and may further incorporate an ionic charging functionality into the SOF network. An SOF including one or more capping segments may also be referred to as capped SOFs. The differences between a SOF and SOFs having capping segments, capping segments having ionic functionality, or molecular building blocks having ionic functionality are illustrated in FIG. 1. FIG. 1 illustrates the differences between a standard structured organic film, a structured organic film having a capping segment, a structured organic film having molecular building block segments with ionic functionality, and a structured organic film having a capping segment with ionic functionality. Various networks of SOFs are shown, wherein a typical SOF network 100A is shown in FIG. 1A, having several segments 102 connected by several linkers 104. Another SOF network 100B is representative of a capped SOF network 100B having several segments 102 connected by several linkers 104, wherein a capping segment 106 closes off or terminates a branch of the segment 102. In SOF network 100C, a plurality of segments having ionic functionality, also referred to as an ionic building block 102A are shown to be connected by linkers 104. In SOF network 100D, a plurality of segments 102 connected by several linkers 104 are illustrated, wherein a capping segment having an ionic group 106A closes off or terminates a branch of the segment 102. Capping segments can be absent an ionic group as in capping segment 106 or have an ionic group as in capping segment 106A, but have only one linking functional group (Fg) that reacts to terminate or close off a branch of a segment 102 of an SOF. The ionic group on a capping segment can have ionic character initially or via a chemical reaction or treatment in a post-processing step after formation of the SOF. Molecular building block segments can be absent an ionic group as in segment 102 or have an ionic group as in ionic building block segment 102A. Molecular building block segments 102, 102A also have more than one linking Fg that reacts with the SOF to form the SOF network. The ionic group on a molecular building block can have ionic character initially or via a chemical reaction or treatment in a post-processing step after formation of the SOF. While the exemplary SOF networks 100A, 100B, 100C, 100D illustrate the inclusion of various components to an SOF network of the present disclosure, they are non-limiting, and certain examples of SOF networks of the present disclosure can have some or all of the various segments, linkers, capping segments, ionic capping segments or capping segments with ionic functional groups, molecular building block segments, ionic molecular building block segments, or combinations thereof.

Capped SOF compositions or SOF compositions having ionic groups in either the segments or molecular building blocks, or capping segments can provide tunable materials whose properties can be varied through the type and amount of ionic groups introduced. Conventional membranes used in IEC or charged membrane applications are typically made by providing a polymer or network backbone, followed by subsequent introduction of a charge functionality. Examples of the present disclosure provide structured organic networks where during synthesis, ionic or charged capping segments or alternatively ionic or charged molecular building blocks are incorporated into the structured organic network. As noted previously, in certain examples, charge can be either present upon network formation or induced after network formation by a chemical reaction or post-processing step such as, but not limited to those as described herein. For purposes of the present disclosure, a capping segment having an ionic group prior to processing or after processing or formation may be referred to as an ionic capping segment. Furthermore, a molecular building block having an ionic group prior to processing or after processing or formation may be referred to as an ionic molecular building block or ionic building block or ionic segment.

In embodiments, the capping segments may have a structure that is unrelated to the structure of any of the molecular building blocks that are added into the SOF formulation, which (after film formation) ultimately becomes the SOF. In other words, a capping segment is the portion of a capping group or capping unit that supports functional groups and comprises atoms that are not associated with functional groups. Further, the composition of a capping segment remains unchanged after SOF formation. In embodiments, the capping segment may be the same as a molecular building block, but only have a single reactive site.

A capping segment molecule has one functional group that has suitable or complementary functional groups (as described above) to participate in a chemical reaction to link to another segment during the SOF forming process. A second chemical moiety may be present that is not suitable or complementary to participate in the specific chemical reaction to link together segments during the SOF forming process and thus cannot bridge any further adjacent molecular building blocks. However, after the SOF is formed such functional groups may be available for further reaction with additional components and thus allowing for the further refining and tuning of the various properties of the formed SOF.

In embodiments, the SOF may comprise a mixture of capping segments, such as any combination of a first capping segment, a second capping segment, a third capping segment, a fourth capping segment, etc., where the structure of the capping segment varies. In embodiments, the structure of a capping segment or a combination of multiple capping segments may be selected to either enhance or attenuate the chemical and physical properties of SOF; or the identity of the chemical moieties or functional group(s) on that are not suitable or complementary to participate in the chemical reaction to link together segments during the SOF forming process may be varied to form a mixture of capping segments. Thus, the type of capping segment introduced into the SOF framework may be selected to introduce or tune a desired property of SOF.

In embodiments, a SOF contains segments, which are not located at the edges of the SOF, that are connected by linkers to at least three other segments and/or capping groups. For example, in embodiments the SOF comprises at least one symmetrical building block selected from the group consisting of ideal triangular building blocks, distorted triangular building blocks, ideal tetrahedral building blocks, distorted tetrahedral building blocks, ideal square building blocks, and distorted square building blocks. In embodiments, Type 2 and 3 SOF s contain at least two segment types, which are not located at the edges of the SOF, where at least one segment type is connected by linkers to at least three other segments and/or capping groups. For example, in embodiments the SOF comprises at least one symmetrical building block selected from the group consisting of ideal triangular building blocks, distorted triangular building blocks, ideal tetrahedral building blocks, distorted tetrahedral building blocks, ideal square building blocks, and distorted square building blocks.

In embodiments, the SOF comprises a plurality of segments, where all segments have an identical structure, and a plurality of linkers, which may or may not have an identical structure, wherein the segments that are not at the edges of the SOF are connected by linkers to at least three other segments and/or capping groups. In embodiments, the SOF comprises a plurality of segments where the plurality of segments comprises at least a first and a second segment that are different in structure, and the first segment is connected by linkers to at least three other segments and/or capping groups when it is not at the edge of the SOF.

In embodiments, the SOF comprises a plurality of linkers including at least a first and a second linker that are different in structure, and the plurality of segments either comprises at least a first and a second segment that are different in structure, where the first segment, when not at the edge of the SOF, is connected to at least three other segments and/or capping groups, wherein at least one of the connections is via the first linker, and at least one of the connections is via the second linker; or comprises segments that all have an identical structure, and the segments that are not at the edges of the SOF are connected by linkers to at least three other segments and/or capping groups, wherein at least one of the connections is via the first linker, and at least one of the connections is via the second linker.

In embodiments, the capping segments have a structure that substantially corresponds to the structure of one of the molecular building blocks (such as the molecular building blocks for SOFs that are detailed in U.S. Pat. Nos. 8,093,347; 8,436,130; 8,357,432; 8,394,495; 8,389,060; 8,318,892; and 9,097,995, which have been incorporated by reference) that is added to the SOF formulation, but one or more of the functional groups present on the building block is either missing or has been replaced with a different chemical moiety or functional group that will not participate in a chemical reaction (with the functional group(s) of the building blocks that are initially present) to link together segments during the SOF forming process.

For example, for a molecular building block, such as tris-(4-hydroxymethyl)triphenylamine:

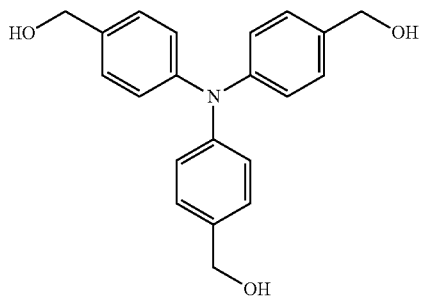 [SMILES: OCc1ccc(N(c2ccc(CO)cc2)c2ccc(CO)cc2)cc1]

among the many possible capping segments that may be used, suitable capping segments may, for example, include:

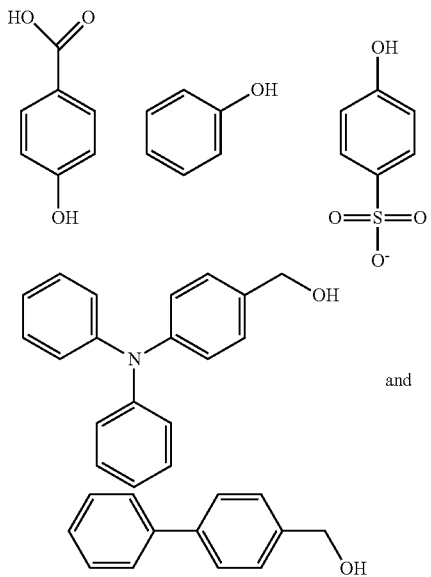

and

A capping group having a structure unrelated to the molecular building block may be, for example, an alkyl moiety (for example, a branched or unbranched saturated hydrocarbon group, derived from an alkane and having the general formula $C_nH_{2n+1}$, in which n is a number of 1 or more) in which one of the hydrogen atoms has been replaced by an —OH group. In such a formulation, a reaction between the capping group and the molecular building block, for example, an acid catalyzed reaction between the alcohol (—OH) groups, would link the capping segment and the molecular building block segments together through the formation of (linking) ether groups. In certain examples, the capping segment can include sulfonic acid, 4-hydroxybenzoic acid, phenol, 4-hydroxybenzenesulfonate, naphthol sulfonic acid, 8-hydroxyquinoline-5-sulfonic acid or a combination thereof. In examples, alternate capping segments can have functional groups that react by condensation of —OH with —COOH, condensation of aldehydes (R—CH=O) and amines yielding imine bonds, aldol condensation between a triazine and aldehyde to form an unsubstituted olefin (—CH=CH—), or combinations thereof.

In embodiments, the capping molecules have one reactive functional group to bond to the SOF network. For example, in embodiments, the capping segments comprise only a single suitable or complementary functional group (as described above) that participates in a chemical reaction to link together segments during the SOF forming process and thus cannot bridge any further adjacent molecular building blocks (until a building block with a suitable or complementary functional group is added, such as when an additional SOF is formed on top of a capped SOF base layer and a multilayer SOF is formed).

When such capping molecules are introduced into the SOF coating formulation, upon curing, interruptions in the SOF framework are introduced. Interruptions in the SOF framework are therefore sites where the single suitable or complementary functional group of the capping molecules have reacted with the molecular building block and locally terminate (or cap) the extension of the SOF framework and interrupt the regular network of covalently bonded building blocks normally present in an SOF. The type of capping segments (or structure of the capping segment) introduced into the SOF framework may be used to tune the properties of the SOF.

In embodiments, the capping segment molecules may comprise more than one chemical moiety or functional group. For example, the SOF coating formulation, which (after film formation), ultimately becomes bonded in the SOF may comprise a capping segment having at least two or more chemical moieties or functional groups, such as 2, 3, 4, 5, 6 or more chemical moieties or functional groups, where only one of the functional groups is a suitable or complementary functional group (as described above) that participates in a chemical reaction to link together segments during the SOF forming process. The various other chemical moieties or functional groups present on the molecular building block are chemical moieties or functional groups that are not suitable or complementary to participate in the specific chemical reaction to link together segments initially present during the SOF forming process and thus cannot bridge any further adjacent molecular building blocks. However, after the SOF is formed such chemical moieties and/or functional groups may be available for further reaction (similar to dangling functional groups, as discussed below) with additional components and thus allow for the further refining and tuning of the various properties of the formed SOF, or chemically attaching various other SOF layers in the formation of multilayer SOFs.

In embodiments, the molecular building blocks may have x functional groups (where x is three or more) and the capping segment molecules may comprise a capping group molecule having one functional group that is suitable or complementary functional group (as described above) and participate in a chemical reaction to link together segments during the SOF forming process. In certain examples, for a Type 1 SOF (single molecular building block type) three or more functional groups are required. For Type 2 SOFs, at least one molecular building block type can have three or more functional groups and the remaining molecular building blocks can have two or more functional groups. For example, x would be three for tris-(4-hydroxymethyl)triphenylamine (above), and x would be four for the building block illustrated below, N,N,N',N'-tetrak:is-[(4-hydroxymethyl)phenyl]-biphenyl-4,4'-diamine:

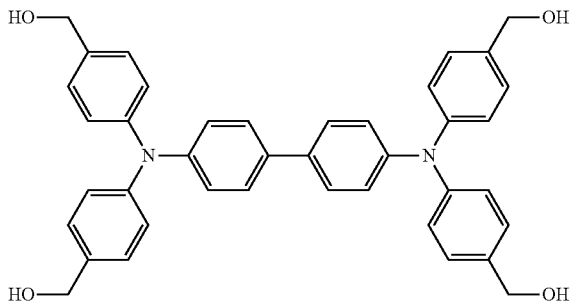 [SMILES: OCc1ccc(N(c2ccc(CO)cc2)c2ccc(-c3ccc(N(c4ccc(CO)cc4)c4ccc(CO)cc4)cc3)cc2)cc1]

Segment

A segment is the portion of the molecular building block that supports functional groups and comprises all atoms that are not associated with functional groups. Further, the composition of a molecular building block segment remains unchanged after SOF formation. In embodiments, the SOF may contain a first segment having a structure the same as or different from a second segment. In other embodiments, the structures of the first and/or second segments may be the same as or different from a third segment, forth segment, fifth segment, etc. A segment is also the portion of the molecular building block that can provide an inclined property. Inclined properties are described later in the embodiments.

In specific embodiments, the segment of the SOF comprises at least one atom of an element that is not carbon, such at least one atom selected from the group consisting of hydrogen, oxygen, nitrogen, silicon, phosphorous, selenium, fluorine, boron, and sulfur.

A description of various exemplary molecular building blocks, linkers, SOF types, strategies to synthesize a specific SOF type with exemplary chemical structures, building blocks whose symmetrical elements are outlined, and classes of exemplary molecular entities and examples of members of each class that may serve as molecular building blocks or other components for SOFs are detailed in U.S. Pat. Nos. 8,093,347; 8,436,130; 8,357,432; 8,394,495; 8,389,060; 8,318,892; and 9,097,995, the disclosures of which are totally incorporated herein by reference in their entireties.

Linker

A linker is a chemical moiety that emerges in a SOF upon chemical reaction between functional groups present on the molecular building blocks and/or capping groups.

A linker may comprise a covalent bond, a single atom, or a group of covalently bonded atoms. The former is defined as a covalent bond linker and may be, for example, a single covalent bond or a double covalent bond and emerges when functional groups on all partnered building blocks are lost entirely. The latter linker type is defined as a chemical moiety linker and may comprise one or more atoms bonded together by single covalent bonds, double covalent bonds, or combinations of the two. Atoms contained in linking groups originate from atoms present in functional groups on molecular building blocks prior to the SOF forming process. Chemical moiety linkers may be well-known chemical groups such as, for example, esters, ketones, amides, imines. ethers, urethanes, carbonates, and the like, or derivatives thereof.

For example, when two hydroxyl (—OH) functional groups are used to connect segments in a SOF via an oxygen atom, the linker would be the oxygen atom, which may also be described as an ether linker. In embodiments, the SOF may contain a first linker having a structure the same as or different from a second linker. In other embodiments, the structures of the first and/or second linkers may be the same as or different from a third linker, etc.

A capping segment may be bonded in the SOF in any desired amount as long as the general SOF framework is sufficiently maintained. For example, in embodiments, a capping segment may be bonded to at least 0.1% of all linkers, but not more than about 40% of all linkers present in an SOF, such as from about 0.5% to about 30%, or from about 2% to about 20%. In embodiments, substantially all segments may be bound to at least one capping segment, where the term "substantially all" refers, for example, to more than about 95%, such as more than about 99% of the segments of the SOF. In the event capping segments bond to more than 50% of the available functional groups on the molecular building blocks (from which the linkers emerge), oligomers, linear polymers, and molecular building blocks that are fully capped with capping segments may predominately form instead of a SOF. In certain examples of SOFs, capping segments may be quantitatively expressed in terms of mol %, concentration, or as ratios compared to either a segment composition or of an entire SOF composition.

In specific embodiments, the linker comprises at least one atom of an element that is not carbon, such at least one atom selected from the group consisting of hydrogen, oxygen, nitrogen, silicon, phosphorous, selenium, fluorine, boron, and sulfur.

Metrical Parameters of SOFs

SOFs have any suitable aspect ratio. In embodiments, SOFs have aspect ratios for instance greater than about 30:1 or greater than about 50:1, or greater than about 70:1, or greater than about 100:1, such as about 1000:1. The aspect ratio of a SOF is defined as the ratio of its average width or diameter (that is, the dimension next largest to its thickness) to its average thickness (that is, its shortest dimension). The term 'aspect ratio,' as used here, is not bound by theory. The longest dimension of a SOF is its length and it is not considered in the calculation of SOF aspect ratio.

Generally, SOFs have widths and lengths, or diameters greater than about 500 micrometers, such as about 10 mm, or 30 mm. The SOFs have the following illustrative thicknesses: about 10 Angstroms to about 250 Angstroms, such as about 20 Angstroms to about 200 Angstroms, for a monosegment thick layer and about 20 nm to about 5 mm, about 50 nm to about 10 mm for a multi-segment thick layer.

SOF dimensions may be measured using a variety of tools and methods. For a dimension about 1 micrometer or less, scanning electron microscopy is the preferred method. For a dimension about 1 micrometer or greater, a micrometer (or ruler) is the preferred method.

Multilayer SOFs

A SOF may comprise a single layer or a plurality of layers (that is, two, three or more layers). SOFs that are comprised of a plurality of layers may be physically joined (e.g., dipole and hydrogen bond) or chemically joined. Physically attached layers are characterized by weaker interlayer interactions or adhesion; therefore physically attached layers may be susceptible to delamination from each other. Chemically attached layers are expected to have chemical bonds (e.g., covalent or ionic bonds) or have numerous physical or intermolecular (supramolecular) entanglements that strongly link adjacent layers.

Therefore, delamination of chemically attached layers is much more difficult. Chemical attachments between layers may be detected using spectroscopic methods such as focusing infrared or Raman spectroscopy, or with other methods having spatial resolution that can detect chemical species precisely at interfaces. In cases where chemical attachments between layers are different chemical species than those within the layers themselves it is possible to detect these attachments with sensitive bulk analyses such as solid-state nuclear magnetic resonance spectroscopy or by using other bulk analytical methods.

In the embodiments, the SOF may be a single layer (mono-segment thick or multi-segment thick) or multiple layers (each layer being mono-segment thick or multi-segment thick). "Thickness" refers, for example, to the smallest dimension of the film. As discussed above, in a SOF, segments are molecular units that are covalently bonded through linkers to generate the molecular framework of the film. The thickness of the film may also be defined in terms of the number of segments that is counted along that axis of the film when viewing the cross-section of the film. A "monolayer" SOF is the simplest case and refers, for example, to where a film is one segment thick. A SOF where two or more segments exist along this axis is referred to as a "multi-segment" thick SOF.

An exemplary method for preparing physically attached multilayer SOFs includes: (1) forming a base SOF layer that may be cured by a first curing cycle, and (2) forming upon the base layer a second reactive wet layer followed by a second curing cycle and, if desired, repeating the second step to form a third layer, a fourth layer and so on. The physically stacked multilayer SOFs may have thicknesses greater than about 20 Angstroms such as, for example, the following illustrative thicknesses: about 20 Angstroms to about 10 mm, such as about 1 nm to about 10 mm, or about 0.1 mm Angstroms to about 5 mm. In principle there is no limit with this process to the number of layers that may be physically stacked. Alternative examples of SOFs according to the present disclosure include free-standing films. The free-standing film thickness can be from about 1 μm to about 500 μm, or from about 10 μm to about 250 μm, or from about 100 μm to about 150 μm.

In embodiments, a multilayer SOF is formed by a method for preparing chemically attached multilayer SOFs by: (1) forming a base SOF layer having functional groups present on the surface (or dangling functional groups) from a first reactive wet layer, and (2) forming upon the base layer a second SOF layer from a second reactive wet layer that comprises molecular building blocks with functional groups capable of reacting with the dangling functional groups on the surface of the base SOF layer. In further embodiments, a capped SOF may serve as the base layer in which the functional groups present that were not suitable or complementary to participate in the specific chemical reaction to link together segments during the base layer SOF forming process may be available for reacting with the molecular building blocks of the second layer to form a chemically bonded multilayer SOF. If desired, the formulation used to form the second SOF layer should comprise molecular building blocks with functional groups capable of reacting with the functional groups from the base layer as well as additional functional groups that will allow for a third layer to be chemically attached to the second layer. The chemically stacked multilayer SOFs may have thicknesses greater than about 20 Angstroms such as, for example, the following illustrative thicknesses: about 20 Angstroms to about 10 mm, such as about 1 nm to about 10 mm, or about 0.1 mm Angstroms to about 5 mm. In principle there is no limit with this process to the number of layers that may be chemically stacked.

In embodiments, the method for preparing chemically attached multilayer SOFs comprises promoting chemical attachment of a second SOF onto an existing SOF (base layer) by using a small excess of one molecular building block (when more than one molecular building block is present) during the process used to form the SOF (base layer) whereby the functional groups present on this molecular building block will be present on the base layer surface. The surface of base layer may be treated with an agent to enhance the reactivity of the functional groups or to create an increased number of functional groups.

In an embodiment the dangling functional groups or chemical moieties present on the surface of an SOF or capped SOF may be altered to increase the propensity for covalent attachment (or, alternatively, to disfavor covalent attachment) of particular classes of molecules or individual molecules, such as SOFs, to a base layer or any additional substrate or SOF layer. For example, the surface of a base layer, such as an SOF layer, which may contain reactive dangling functional groups, may be rendered pacified through surface treatment with a capping chemical group. For example, a SOF layer having dangling hydroxyl alcohol groups may be pacified by treatment with trimethylsilylchloride thereby capping hydroxyl groups as stable trimethylsilylethers. Alternatively, the surface of base layer may be treated with a non-chemically bonding agent, such as a wax, to block reaction with dangling functional groups from subsequent layers.

Molecular Building Block Symmetry

Molecular building block symmetry relates to the positioning of functional groups (Fgs) around the periphery of the molecular building block segments. Without being bound by chemical or mathematical theory, a symmetric molecular building block is one where positioning of Fgs may be associated with the ends of a rod, vertexes of a regular geometric shape, or the vertexes of a distorted rod or distorted geometric shape. For example, the most symmetric option for molecular building blocks containing four Fgs are those whose Fgs overlay with the corners of a square or the apexes of a tetrahedron.

Use of symmetrical building blocks is practiced in embodiments of the present disclosure for two reasons: (1) the patterning of molecular building blocks may be better anticipated because the linking of regular shapes is a better understood process in reticular chemistry, and (2) the complete reaction between molecular building blocks is facilitated because for less symmetric building blocks errant conformations/orientations may be adopted which can possibly initiate numerous linking defects within SOFs.

In embodiments, a Type 1 SOF contains segments, which are not located at the edges of the SOF, that are connected by linkers to at least three other segments. For example, in embodiments the SOF comprises at least one symmetrical building block selected from the group consisting of ideal triangular building blocks, distorted triangular building blocks, ideal tetrahedral building blocks, distorted tetrahedral building blocks, ideal square building blocks, and distorted square building blocks. In embodiments, Type 2 and 3 SOFs contains at least one segment type, which are not located at the edges of the SOF, that are connected by linkers to at least three other segments. For example, in embodiments the SOF comprises at least one symmetrical building block selected from the group consisting of ideal triangular building blocks, distorted triangular building blocks, ideal tetrahedral building blocks, distorted tetrahedral building blocks, ideal square building blocks, and distorted square building blocks.

Practice of Linking Chemistry

In embodiments linking chemistry may occur wherein the reaction between functional groups produces a volatile byproduct that may be largely evaporated or expunged from the SOF during or after the film forming process or wherein no byproduct is formed. Linking chemistry may be selected to achieve a SOF for applications where the presence of linking chemistry byproducts is not desired. Linking chemistry reactions may include, for example, condensation, addition/elimination, and addition reactions, such as, for example, those that produce esters, imines, ethers, carbonates, urethanes, amides, acetals, and silyl ethers.

In embodiments the linking chemistry via a reaction between function groups producing a non-volatile byproduct that largely remains incorporated within the SOF after the film forming process. Linking chemistry in embodiments may be selected to achieve a SOF for applications where the presence of linking chemistry byproducts does not impact the properties or for applications where the presence of linking chemistry byproducts may alter the properties of a SOF (such as, for example, the electroactive, hydrophobic or hydrophilic nature of the SOF). Linking chemistry reactions may include, for example, substitution, metathesis, and metal catalyzed coupling reactions, such as those that produce carbon-carbon bonds.

For all linking chemistry the ability to control the rate and extent of reaction between building blocks via the chemistry between building block functional groups is an important aspect of the present disclosure. Reasons for controlling the rate and extent of reaction may include adapting the film forming process for different coating methods and tuning the microscopic arrangement of building blocks to achieve a periodic SOF, as defined in earlier embodiments.

Innate Properties of COFs

COFs have innate properties such as high thermal stability (typically higher than 400° C. under atmospheric conditions); poor solubility in organic solvents (chemical stability), and porosity (capable of reversible guest uptake). In embodiments, SOFs may also possess these innate properties.

Added Functionality of SOFs

Added functionality denotes a property that is not inherent to conventional SOFs and may occur by the selection of molecular building blocks wherein the molecular compositions provide the added functionality in the resultant SOF. Added functionality may arise upon assembly of molecular building blocks and/or capping groups having an "inclined property" for that added functionality. Added functionality may also arise upon assembly of molecular building blocks having no "inclined property" for that added functionality but the resulting SOF has the added functionality as a consequence of segments (S) and linkers in a SOF. In embodiments, added functionality may also arise upon the addition and assembly of molecular building blocks and capping groups having no "inclined property" for that added functionality but the resulting SOF has the added functionality as a consequence of segments and linkers into a SOF. Furthermore, emergence of added functionality may arise from the combined effect of using molecular building blocks bearing an "inclined property" for that added functionality whose inclined property is modified or enhanced upon linking together the segments and linkers into a SOF.

An Inclined Property of a Molecular Building Block Segment

The term "inclined property" of a molecular building block refers, for example, to a property known to exist for certain molecular compositions or a property that is reasonably identifiable by a person skilled in art upon inspection of the molecular composition of a segment. As used herein, the terms "inclined property" and "added functionality" refer to the same general property (e.g., hydrophobic, electroactive, etc.) but "inclined property" is used in the context of the molecular building block and "added functionality" is used in the context of the SOF.

The hydrophobic (superhydrophobic), hydrophilic, lipophobic (superlipophobic), lipophilic, photochromic and/or electroactive (conductor, semiconductor, charge transport material) nature of an SOF are some examples of the properties that may represent an "added functionality" of an SOF. These and other added functionalities may arise from the inclined properties of the molecular building blocks or may arise from building blocks that do not have the respective added functionality that is observed in the SOF.

The term hydrophobic (superhydrophobic) refers, for example, to the property of repelling water, or other polar species such as methanol, it also means an inability to absorb water and/or to swell as a result. Furthermore, hydrophobic implies an inability to form strong hydrogen bonds to water or other hydrogen bonding species. Hydrophobic materials are typically characterized by having water contact angles greater than 90° and superhydrophobic materials have water contact angles greater than 150° as measured using a contact angle goniometer or related device.

The term hydrophilic refers, for example, to the property of attracting, adsorbing, or absorbing water or other polar species, or a surface that is easily wetted by such species. Hydrophilic materials are typically characterized by having less than 20° water contact angle as measured using a contact angle goniometer or related device. Hydrophilicity may also be characterized by swelling of a material by water or other polar species, or a material that can diffuse or transport water, or other polar species, through itself. Hydrophilicity, is further characterized by being able to form strong or numerous hydrogen bonds to water or other hydrogen bonding species.

The term lipophobic (oleophobic) refers, for example, to the property of repelling oil or other non-polar species such as alkanes, fats, and waxes. Lipophobic materials are typically characterized by having oil contact angles greater than 90° as measured using a contact angle goniometer or related device.

The term lipophilic (oleophilic) refers, for example, to the property attracting oil or other non-polar species such as alkanes, fats, and waxes or a surface that is easily wetted by such species. Lipophilic materials are typically characterized by having a low to nil oil contact angle as measured using, for example, a contact angle goniometer. Lipophilicity can also be characterized by swelling of a material by hexane or other non-polar liquids.

The term photochromic refers, for example, to the ability to demonstrate reversible color changes when exposed to electromagnetic radiation. SOF compositions containing photochromic molecules may be prepared and demonstrate reversible color changes when exposed to electromagnetic radiation. These SOFs may have the added functionality of photochromism. The robustness of photochromic SOFs may enable their use in many applications, such as photochromic SOFs for erasable paper, and light responsive films for window tinting/shading and eyewear. SOF compositions may contain any suitable photochromic molecule, such as a difunctional photochromic molecules as SOF molecular building blocks (chemically bound into SOF structure), a monofunctional photochromic molecules as SOF capping segments (chemically bound into SOF structure, or unfunctionalized photochromic molecules in an SOF composite (not chemically bound into SOF structure). Photochromic SOFs may change color upon exposure to selected wavelengths of light and the color change may be reversible.

SOF compositions containing photochromic molecules that chemically bond to the SOF structure are exceptionally chemically and mechanically robust photochromic materials. Such photochromic SOF materials demonstrate many superior properties, such as high number of reversible color change processes, to available polymeric alternatives.

SOFs having a rough, textured, or porous surface on the sub-micron to micron scale may be hydrophobic. The rough, textured, or porous SOF surface can result from dangling functional groups present on the film surface or from the structure of the SOF. The type of pattern and degree of patterning depends on the geometry of the molecular building blocks and the linking chemistry efficiency. The feature size that leads to surface roughness or texture is from about 100 nm to about 10 μm, such as from about 500 nm to about 5 μm. The feature size that leads to an SOF porosity is from about 5 nm to about 2500 nm, such as from about 50 nm to about 1000 nm, as measured by SEM cross-sectional images. In certain examples, porosity can be also be in a range of 0.1 nm to 2500 nm for aggregated COFs below the SOF film, as visually quantified by SEM cross-sectional images. Microscopy can provide a method for the analysis of pore geometry and sizes in the mesopore range or above via direct observations of thin cross-sections of solid materials. Depending on the specific pore-size resolution required, optical or electron microscopy can be used.

Process for Preparing a Gradient Structured Organic Film (SOF)

The process for making gradient SOFs (which may be referred to as an "SOF" below) typically comprises a similar number of activities or steps (set forth below) that are used to make a non-gradient SOF. The capping group may be added during either step a, b or c depending the desired distribution of the capping segment in the resulting SOF. For example, if it is desired that the capping segment distribution is substantially uniform over the resulting SOF, the capping segment may be added during step a). Alternatively, if, for example, a more heterogeneous distribution of the capping segment is desired, as in the case of a gradient SOF, the reactivity of the capping group functional group is lower than that of the functional groups of the molecular building blocks. Alternatively, if, for example, a more heterogeneous distribution of the capping segment is desired, adding the capping segment (such as by spraying it on the film formed during step b or during the promotion step of step c) may occur during steps b and c. Alternatively, the ionic segment may be innately ionic, or can be subjected to an additional post-processing step, e.g., after step c) to add or react with a capping segment or molecular building block to provide an ionic group.

The process for making SOFs typically comprises a number of activities or steps (set forth below) that may be performed in any suitable sequence or where two or more activities are performed simultaneously or in close proximity in time:

A process for preparing a structured organic film comprising:
(a) preparing a liquid-containing reaction mixture comprising a plurality of molecular building blocks each comprising a segment and a number of functional groups;
(b) depositing the reaction mixture as a wet film;
(c) promoting a change of the wet film including the molecular building blocks to a dry film comprising the SOF comprising a plurality of the segments and a plurality of linkers arranged as a covalent organic framework, wherein at a macroscopic level the covalent organic framework is a film;
(d) optionally removing the SOF from the coating substrate to obtain a free-standing SOF;
(e) optionally processing the free-standing SOF into a roll;
(f) optionally cutting and seaming the SOF into a belt; and
(g) optionally performing the above SOF formation process(es) upon an SOF (which was prepared by the above SOF formation process(es)) as a substrate for subsequent SOF formation process(es).

The above activities or steps may be conducted at atmospheric, super atmospheric, or subatmospheric pressure. The term "atmospheric pressure" as used herein refers to a pressure of about 760 torr. The term super atmospheric, refers to pressures greater than atmospheric pressure, but less than 20 atm. The term "subatmospheric pressure" refers to pressures less than atmospheric pressure. In an embodiment, the activities or steps may be conducted at or near atmospheric pressure. Generally, pressures of from about 0.1 atm to about 2 atm, such as from about 0.5 atm to about 1.5 atm, or 0.8 atm to about 1.2 atm may be conveniently employed. Further considerations related to the aforementioned process steps or processes for preparing or fabricating SOFs are detailed in U.S. Pat. Nos. 8,093,347; 8,436,130; 8,357,432; 8,394,495; 8,389,060; 8,318,892; and 9,097,995, the disclosures of which are totally incorporated herein by reference in their entireties.

Figure 2:
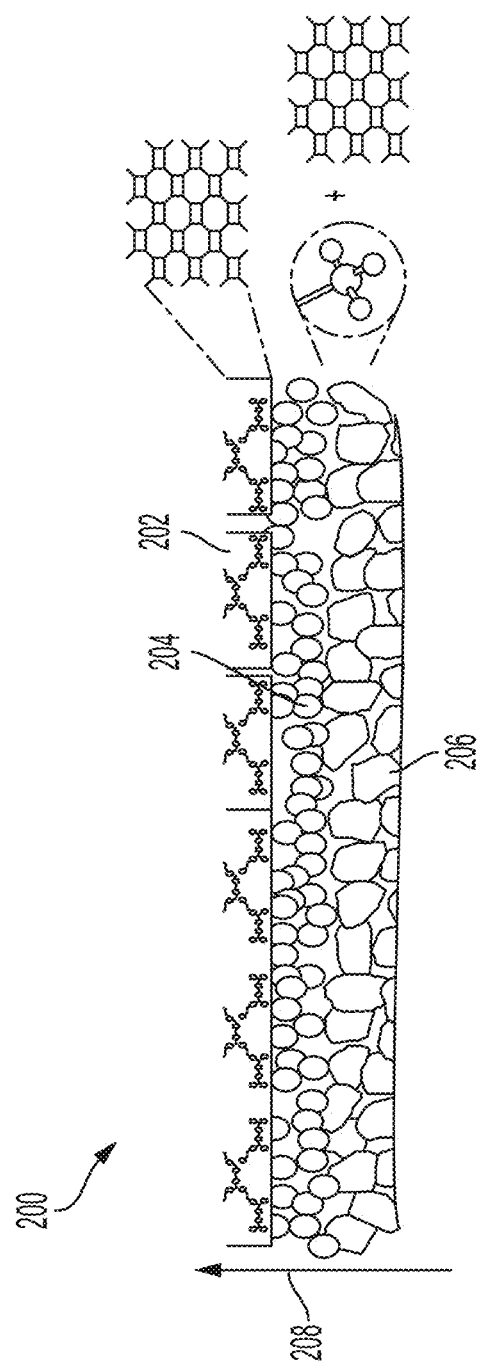
FIG. 2 represents a simplified side view of an exemplary membrane that incorporates a SOF of the present disclosure.

FIG. 2 represents a simplified side view of an exemplary membrane that incorporates a SOF of the present disclosure. A schematic representation of a high-quality free standing film with tunable thickness exhibiting controlled mesoporosity varies gradually from porous voids to a dense surface film is shown. While the film includes a total concentration of capping segments having an acid functional group, for example, a sulfonic acid functional group, a concentration gradient of building blocks within the SOF network transition from ionically charged building blocks or segments to non-ionically charged building blocks or segments. The charge density varies along the films depth as seen in FIG. 2 as well. By taking advantage of this concentration gradient, the properties of the SOF films can be tailored to enhance characteristics such as wettability, charge transport, mechanical, optical and thermal properties as well as the density of key functional groups. A structured organic film (SOF), including a plurality of segments, a plurality of linkers, and a plurality of capping segments is shown. The capping segments include sulfonic acid species, which are incorporated into the SOF as the SOF is fabricated. A first edge or surface has a higher segment to capping segment ratio at a first edge or surface of the SOF as compared to the segment to capping segment ratio at a second edge or surface of the SOF. In alternate examples, there may be a higher segment to capping segment ratio at the second edge or surface of the SOF as compared to the segment to capping segment ratio at the first edge or surface of the SOF. Further, while examples exhibit capping segments having a sulfonic acid functionality, other functional groups such as nitrogen functional groups like amino (—$NH_2$), carboxylic acid groups, phosphonic acid groups. Illustrative examples of capping segments include sulfonic acid, 4-hydroxybenzoic acid, phenol, 4-hydroxybenzenesulfonate, naphthol sulfonic acid, 8-hydroxyquinoline-5-sulfonic acid or a combination thereof. The feature size that leads to an SOF porosity is from about 5 nm to about 2500 nm, such as from about 50 nm to about 1000 nm, as measured by SEM cross-sectional images.

Examples of the present disclosure include various CEM and AEM-type SOFs which have been made to evaluate the ion exchange capacity (IEC) of these materials. The IEC is a parameter that provides the number of cationic groups for AEMs or the number of anionic groups for CEMs based on number of equivalents (frequently milliequivalents) per gram of dry membrane. IEC is an ion-exchange capacity, also referred to as a charge per mass of polymer expressed either in milliequivalents of charge per gram of polymer, meq/g. In certain examples, a doubly charged ion within the polymer has twice the equivalents of charge as compared to a singly charged ion.

As described herein, a variety of ionic molecules, or ionic molecule precursors, that can be used as molecular building blocks or capping groups. In the present examples, a cationic or anionic species from Table 1 with one of the two aromatic building block molecules (THM-TBD or TME-TBD) as described previously. The reaction mechanisms employed in the examples are based on the formation of ether linkages (transetherification) but the reaction linkages can be extended to B—O (boroxine, boronate ester, spiroborate, and borosilicate), C—N (imine, hydrazone, and squaraine), C—N(β-ketoenamine, imide, and amide), in other examples.

Examples

Comparative Example 1 describes the synthesis of a THM-TBD (N,N,N',N'-tetrakis-[(4-hydroxymethyl) phenyl]-biphenyl-4,4'-diamine) based SOF without any ionic groups, as shown in the following generalized reaction scheme:

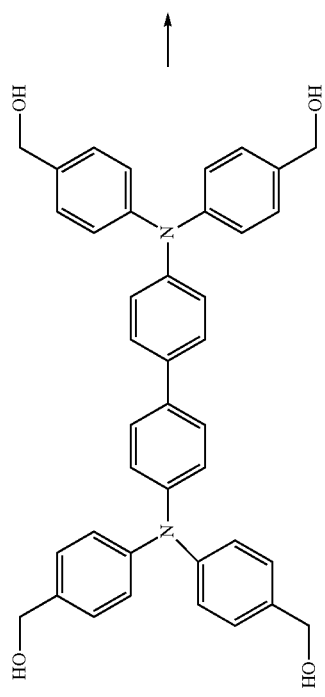

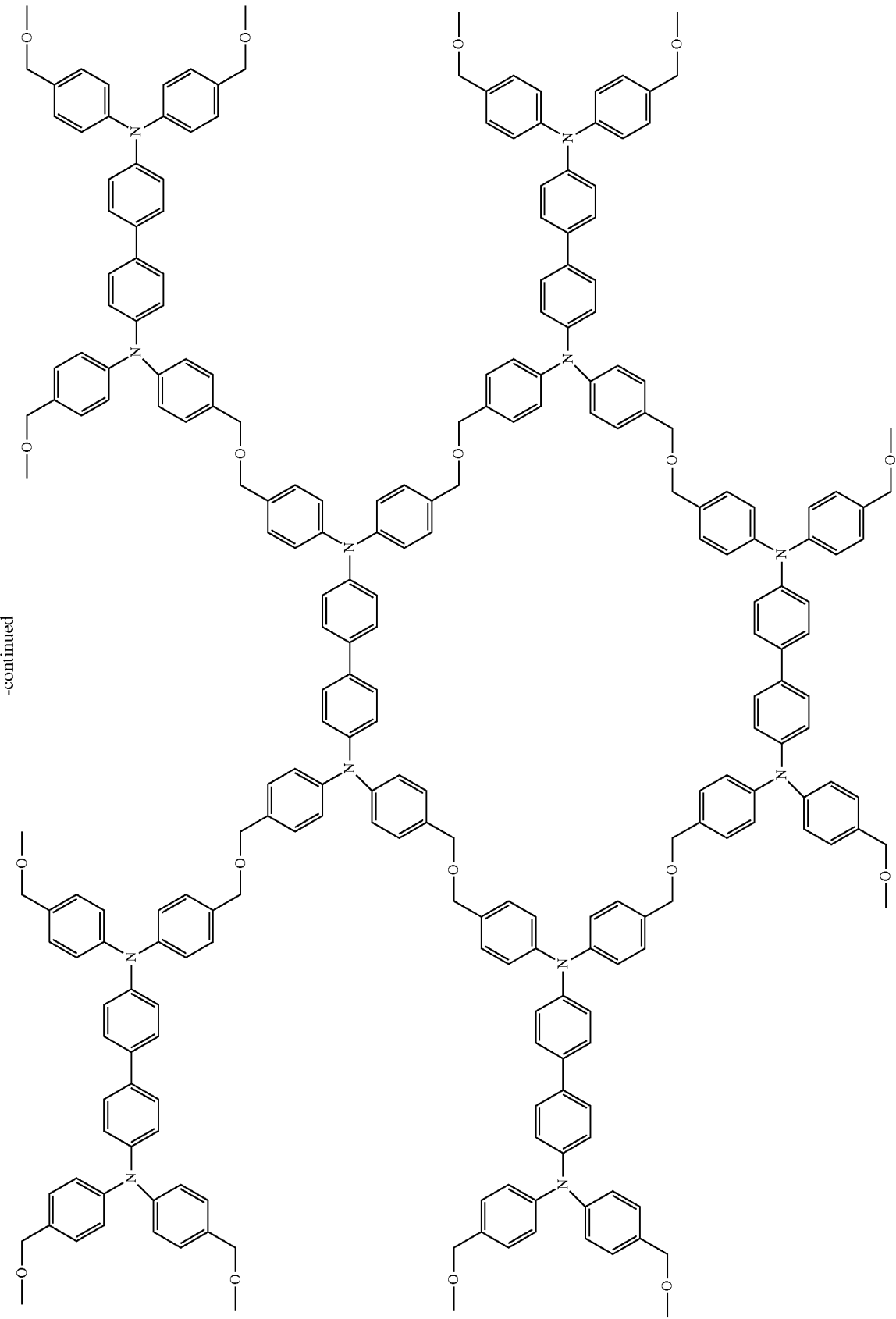

A liquid reaction mixture was prepared by adding the following components to a 10 mL vial to form a 10% solid solution of pre-reacted THM-TBD—Cymel 303 (0.0103 g, 1 wt. %), Dowanol PM (9.0122 g), Nacure 5225 (0.0099 g, 0.25 wt. %), Silclean 3700 (0.0444 g, 1 wt. %) and THM-TBD (0.9784 g, 97.75 wt. %). After adding all the components, the vial was mixed vigorously by shaking. The vial was then placed in a vial block heater at 65° C. for 90 minutes.

Figure 3:
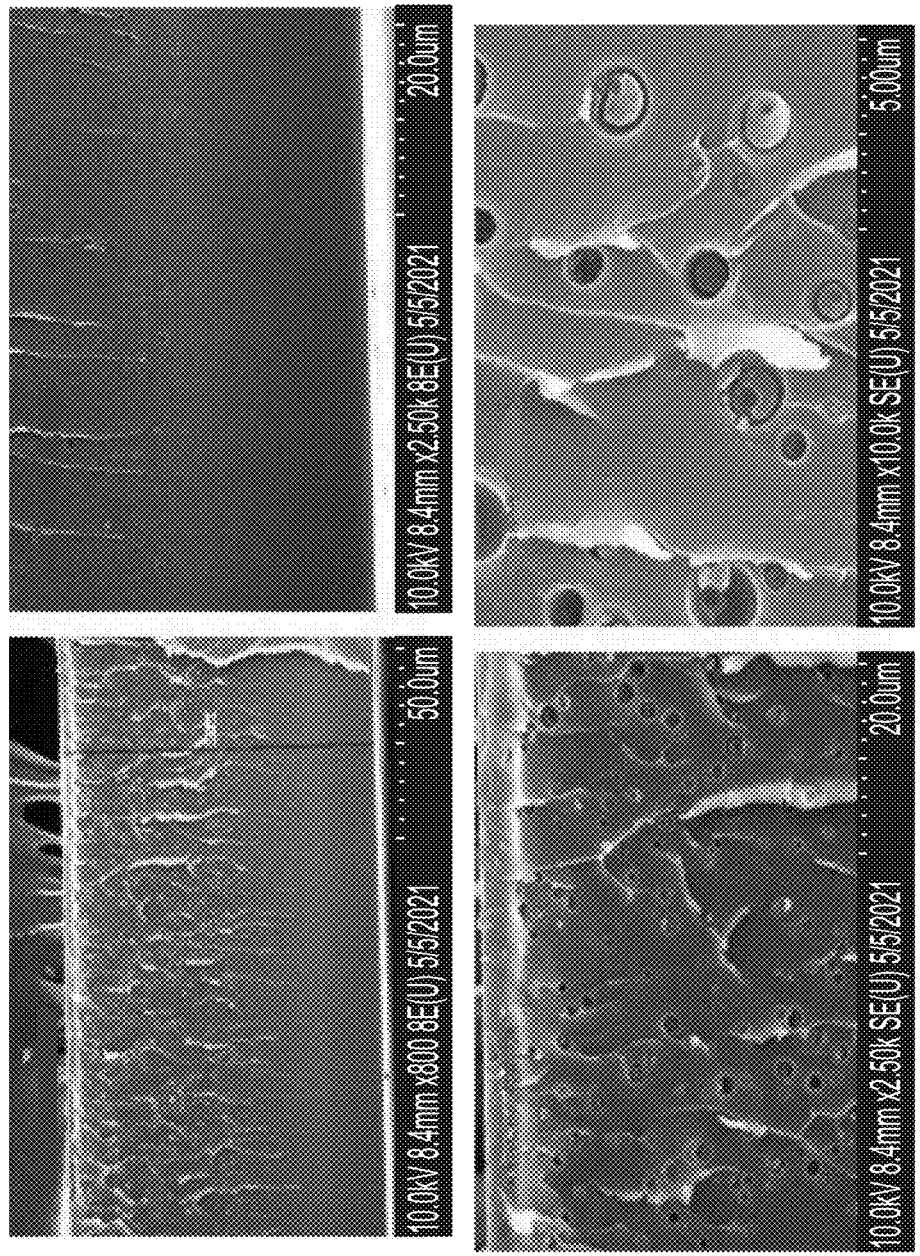
FIG. 3 represents a series of photographs exhibiting a comparative example in cross-section at several magnifications in accordance with the present disclosure.

FIG. 3 represents a series of photographs exhibiting a comparative example in cross-section at several magnifications in accordance with the present disclosure. The scanning electron microscope (SEM) photographic cross-sections show a fairly homogeneous structure with the lower region appearing more featureless than the top region. The film does begin to show a porous region towards the upper section of the film most likely due to the channeling and evaporation of the Dowanol PM solvent.

Several examples related to porous functionally gradient SOFs according to the present disclosure have been synthesized with THM-TBD reacted 4-hydroxybenzene sulfonic acid (4HBenSA) as shown in the following generalized partial reaction scheme:

used. This ratio or concentration of capping segments to segments can be from about 0.5, to about 10.0, or from about 1.0 to about 5.0, or from about 1.0 to about 2.5. Molar equivalents of ionic capping segments as compared to non-ionic segments can also be from about 0.5, to about 10.0, or from about 1.0 to about 5.0, or from about 1.0 to about 2.5. The upper limit of ionic capping group segments depends on the number of reactive functional group sites on a given molecular building block segment. It cannot exceed n-2, where n is the number of reactive functional groups on a molecular building block segment, otherwise a linear polymer or small molecules can form.

TABLE 1

THM-TBD anionic films showing thickness measurements as measured by a Heidenhain thickness probe.

| Example | 4HBenSA Equivalent | Film Thickness |
|---------|--------------------|----------------|
| 1       | 1.0 eq.            | 150 μm         |
| 2       | 0.5 eq.            | 100-150 μm     |
| 3       | 1.5 eq.            | 150 μm         |

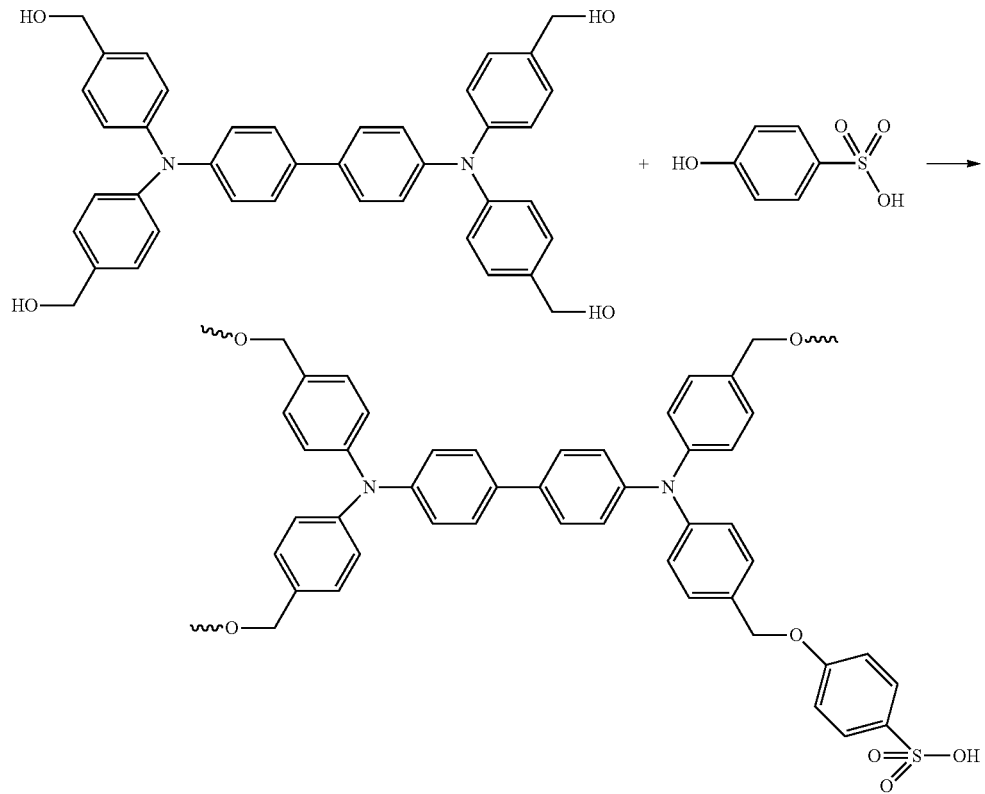

Figure 4:
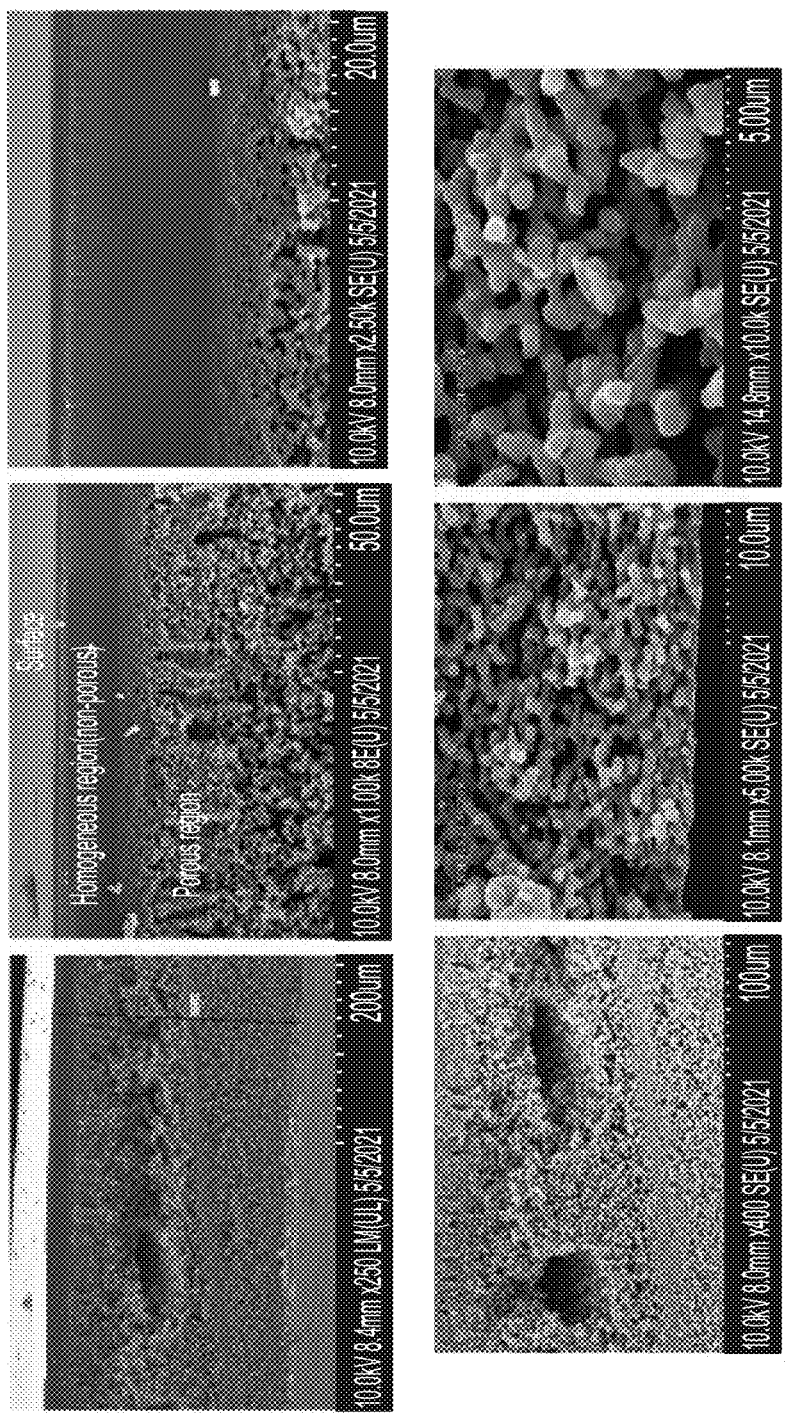
FIG. 4 represents a series of photographs exhibiting a porosity gradient in cross-section in an SOF of the present disclosure.

Three films, cured at 120° C. for 40 min, as shown in Table 1, containing a concentration of 0.5, 1.0, and 1.5 molar equivalents of 4-hydroxybenzene sulfonic acid were synthesized to demonstrate the gradient effect of adding an ionic species to the THM-TBD network. A molar equivalent is a ratio of moles of a capping segment, 4-hydroxybenzene sulfonic acid in examples as described herein, to moles of a molecular building block, such as THM-TBD in this example. In alternate examples, other capping segments having acid-functional groups or other ionic groups can be FIG. 4 represents a series of photographs exhibiting a porosity gradient in cross-section in an SOF of the present disclosure. To fabricate Example 1, as shown in FIG. 4, a liquid reaction mixture was prepared by adding the following components to a 10 mL vial to form a 10% solid solution of pre-reacted THM-TBD and 4HBenSA, containing 1.0 eq. 4HBenSA: Dowanol PM (9.0115 g), Silclean 3700 (0.0455 g, 1 wt. %) and THM-TBD (0.7728 g, 76.98 wt. %). After adding all the components, the vial was mixed periodically while heating in a vial block heater at 65° C. for 90 minutes.

Once the solution was completely dissolved, it was left to cool to room temperature. The solution can alternatively be left overnight before adding the 4-hydroxybenzene sulfonic acid (0.2273 g, 22.02 wt. %) or else added after reaching ambient temperature and coated immediately into an aluminum pan or other suitable substrate. FIG. 4 clearly shows the transition of a porous region in film to a homogeneous, non-porous region. The SEM-EDS analysis of the porous region confirms the presence of carbon, oxygen and sulfur, where the sulfur content from 4HBenSA was approximately 4.7%. As the amount of 4HBenSA is increased in the formulation, the evidence and magnitude of porous particulate is very clear.

Figure 5:
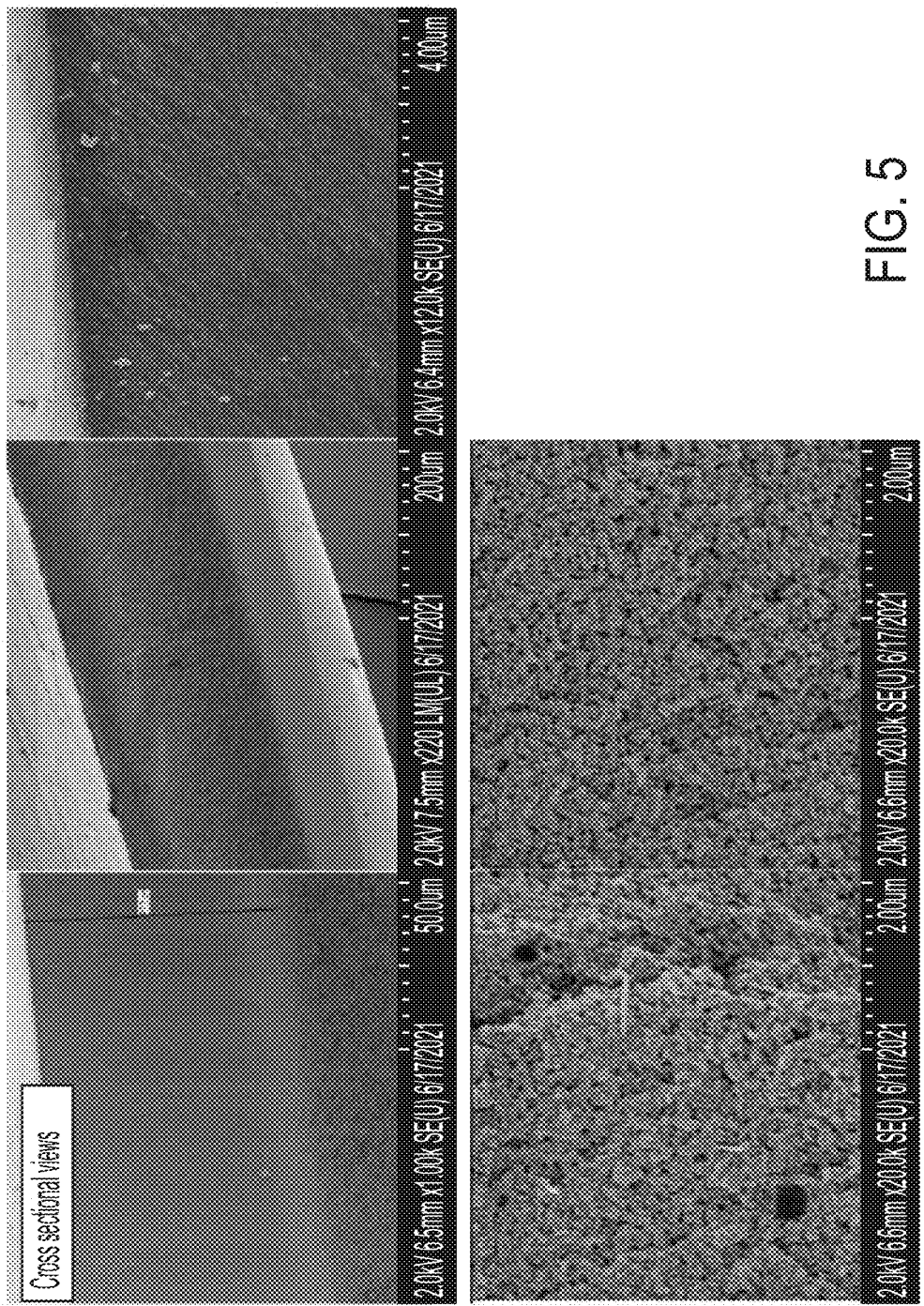
FIG. 5 represents a series of photographs exhibiting a porosity gradient in cross-section at several magnifications at several magnifications in an SOF of the present disclosure.

FIG. 5 represents a series of photographs exhibiting a porosity gradient in cross-section at several magnifications in an SOF of the present disclosure. To fabricate Example 2, as shown in FIG. 5, a liquid reaction mixture was prepared by adding the following components to a 10 mL vial to form a 10% solid solution of pre-reacted THM-TBD and 4HBenSA, containing 0.5 eq. 4HBenSA: Dowanol PM solvent (9.0027 g), Silclean 3700 (0.0493 g, 1 wt. %) and THM-TBD (0.8704 g, 86.61 wt. %). After adding all the components, the vial was mixed periodically while heating in a vial block heater at 65° C. for 90 minutes. Once the solution was completely dissolved, it was left to cool to room temperature. The solution can be left overnight before adding the 4-hydroxybenzene sulfonic acid (0.1282 g, 12.39 wt. %) or alternatively added after reaching ambient temperature and coated immediately into an aluminum pan or other substrate. SEM cross sectional images (cut with a blade) of Example 2, containing 0.5 eq. of anionic species, show a thickness of the THM-TBD homogeneous gradient portion is approximately 57 microns before transitioning to a porous region which is rich in 4-hydroxybenzene sulfonic acid.

Figure 6:
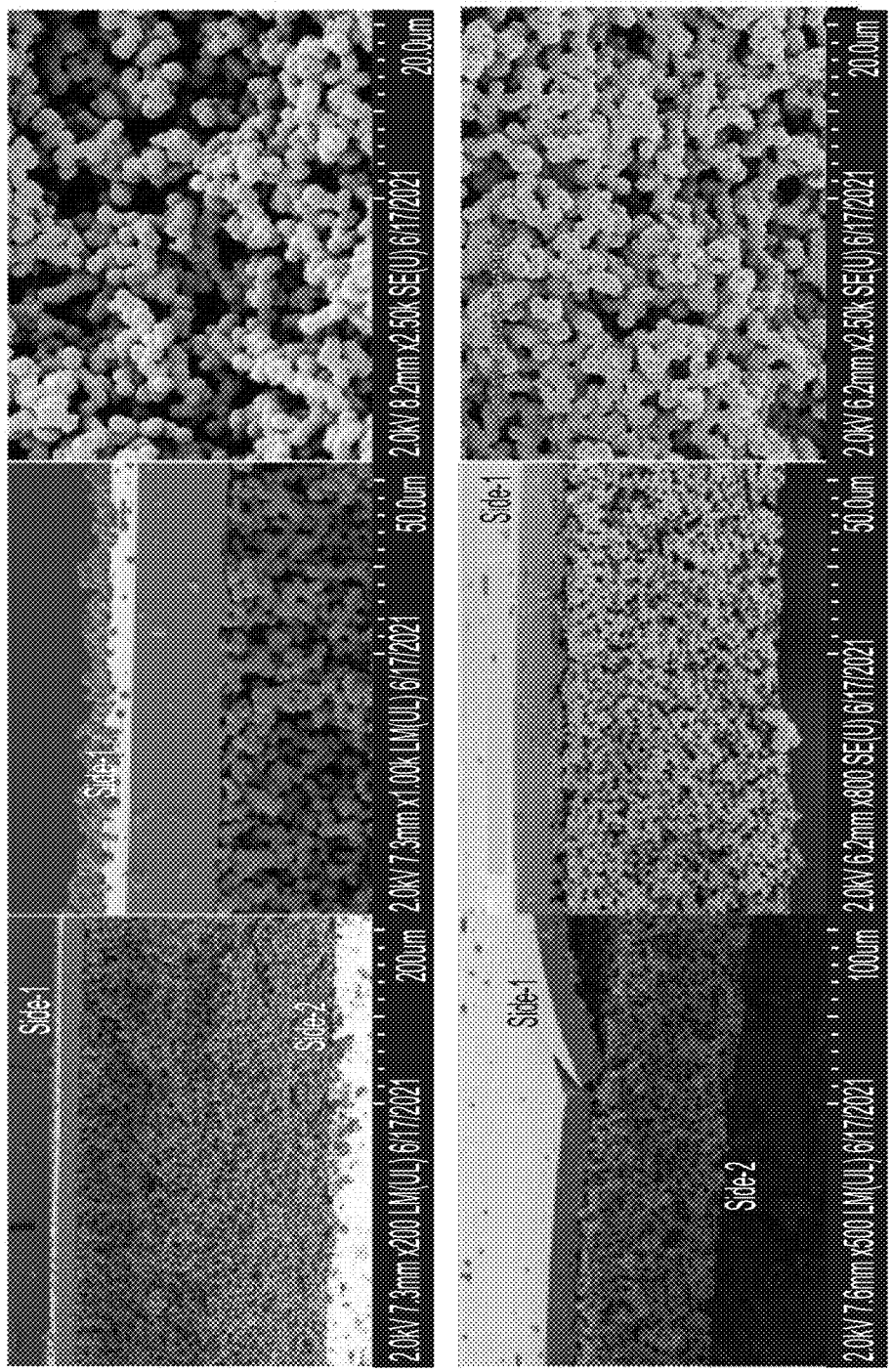
FIG. 6 represents a series of photographs exhibiting a porosity gradient in cross-section at several magnifications in an SOF of the present disclosure.

FIG. 6 represents a series of photographs exhibiting a porosity gradient in cross-section at several magnifications in an SOF of the present disclosure. To fabricate Example 3, as shown in FIG. 6, a liquid reaction mixture was prepared by adding the following components to a 10 mL vial to form a 10% solid solution of pre-reacted THM-TBD and 4HBenSA, containing 1.5 eq. 4HBenSA: Dowanol PM (9.0247 g), Silclean 3700 (0.0412 g, 1 wt. %) and THM-TBD (0.6966 g, 69.27 wt. %). After adding all the components, the vial was mixed periodically while heating in a vial block heater at 65° C. for 90 minutes. Once the solution was completely dissolved, it was left to cool to room temperature. The solution can alternatively be left overnight before adding the 4-hydroxybenzene sulfonic acid (0.3193 g, 29.73 wt. %) or else added after reaching ambient temperature and coated immediately into an aluminum pan or onto an alternate suitable substrate. SEM cross sectional images (cut with a blade) of Example 3, containing 1.5 eq. of anionic species, THM-TBD rich area is the non-porous portion of the cross-section, while the highly particulate, porous region is rich in 4-hydroxybenzene sulfonic acid.

Examples of the present disclosure provide self-standing or free-standing SOF membranes containing ionic species as functional capping segments from about 0.1 to about 1.5 eq. relative to the THM-TBD segment of the SOF, or from about 0.3 eq. to about 8 eq. of 4HBenSA to THM-TBD, or from about 0.5 eq. to about 5 eq. of 4HBenSA to THM-TBD. Ionic species within the SOF can include anionic and cationic functional building blocks containing 1 reactive substituent such as alcohol (—OH) groups that can react with a nonionic component molecule building blocks such as THM-TBD which contains four alcohol (—OH) groups, which can be linked by an acid catalyzed/non-catalyzed transetherification reaction. Further examples include alternating the sulfonic acid capping segments with 4-hydroxybenzoic acid or for non-ionic compositions capping groups such as phenol and alkyl-substituted phenols can be used. SOFs of the present disclosure provide films exhibiting a homogenous THM-TBD rich top layer that transitions to, porous structure as ion concentration increases. The density also decreases as ionic species increases. Similar to biomaterials with functional gradients, these materials can show enhanced mechanical functions as well as non-mechanical functions such as mass transport and energy transformation properties in SOFs. Applications of SOFs of the present disclosure include materials for use in gas selectivity and permeability, storage of gases, liquid molecule separation, catalysis, drug delivery, sensors, energy storage, molecular sieves, electrochemical membranes, fuel cells, energy conversion, and batteries.

While the present teachings have been illustrated with respect to one or more implementations, alterations and/or modifications may be made to the illustrated examples without departing from the spirit and scope of the appended claims. For example, it may be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or embodiments of the present teachings. It may be appreciated that structural objects and/or processing stages may be added, or existing structural objects and/or processing stages may be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items may be selected. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "conformal" describes a coating material in which angles of the underlying material are preserved by the conformal material. The term "about" indicates that the value listed may be somewhat altered, as long as the alteration does not result in nonconformance of the process or structure to the illustrated embodiment. The terms "couple," "coupled," "connect," "connection," "connected," "in connection with," and "connecting" refer to "in direct connection with" or "in connection with via one or more intermediate elements or members." Finally, the terms "exemplary" or "illustrative" indicate the description is used as an example, rather than implying that it is an ideal. Other embodiments of the present teachings may be apparent to those skilled in the art from consideration of the specification and practice of the disclosure herein. It is intended that the specification and examples be considered as exemplary only, with a true scope and spirit of the present teachings being indicated by the following claims.

What is claimed is:

1. A structured organic film (SOF), comprising:
   a plurality of segments;
   a plurality of linkers;
   a plurality of capping segments;
   a first surface of the SOF; and
   a parallel second surface of the SOF connected to the first surface by a thickness of the SOF, wherein:
      a segment to capping segment ratio is greater at the first surface as compared to the parallel second surface; and
      at least one of the plurality of capping segments comprises:

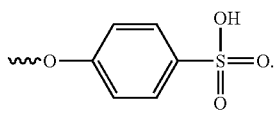

2. The structured organic film (SOF) of claim 1, wherein at least one of the plurality of capping segments is connected through linkers to at least one of the plurality of segments.

3. The structured organic film (SOF) of claim 1, wherein at least one of the plurality of segments comprises:

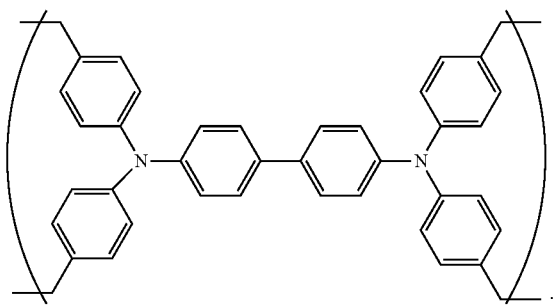

4. The structured organic film (SOF) of claim 1, wherein a concentration of capping segments in the SOF is from about 0.1 to about 5.0 molar equivalents of capping segments as compared to a concentration of segments in the SOF.

5. The structured organic film (SOF) of claim 1, wherein at least one of the plurality of segments comprises an ionic functional group.

6. The structured organic film (SOF) of claim 1, wherein at least one of the plurality of capping segments further comprises an acid-functional group.

7. The structured organic film (SOF) of claim 1, wherein at least one of the plurality of capping segments further comprises a sulfonic acid.

8. The structured organic film (SOF) of claim 1, wherein at least one of the plurality of capping segments further comprises 4-oxybenzoic acid.

9. The structured organic film (SOF) of claim 1, wherein at least one of the plurality of capping segments further comprises oxybenzene.

10. A membrane, comprising:
    a free standing film comprising a first surface and a second surface, comprising:
       a plurality of segments;
       a plurality of linkers; and
       a plurality of capping segments; and
    wherein at least one of the plurality of capping segments comprises:

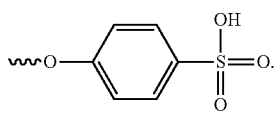

11. The membrane of claim 10, wherein a segment to capping segment ratio is greater at the first surface as compared to the second surface.

12. The membrane of claim 10, wherein a segment to capping segment ratio is smaller at the first surface as compared to the second surface.

13. The membrane of claim 10, wherein at least one of the plurality of segments comprises:

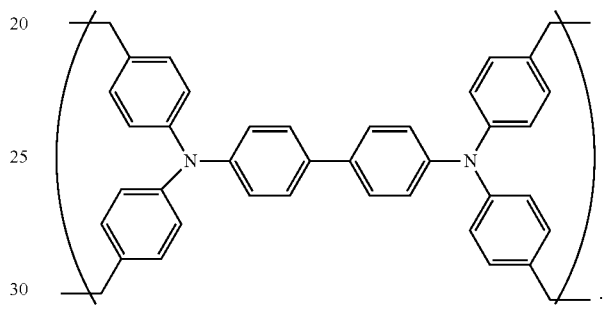

14. The membrane of claim 10, wherein at least one of the plurality of capping segments further comprises a sulfonic acid.

15. The membrane of claim 10, wherein the capping segments of the plurality of capping segments comprise ionic capping segments and nonionic capping segments, wherein a concentration of ionic capping segments in the membrane is from about 0.1 to about 5.0 molar equivalents of ionic capping segments as compared to a total concentration of nonionic segments in the membrane.

16. The membrane of claim 10, wherein a free-standing film thickness is from about 100 nm to about 500 μm.

17. A structured organic film (SOF) membrane, comprising:
    a plurality of segments;
    a plurality of linkers;
    a plurality of capping segments comprising ionic capping segments and nonionic capping segments;
    a first surface of the SOF;
    a second surface of the SOF, wherein:
       a segment to capping segment ratio is greater at the first surface as compared to the second surface; and
       a concentration of ionic capping segments in the SOF is from about 0.1 to about 5.0 molar equivalents of ionic capping segments as compared to a total concentration of nonionic segments in the SOF; and
    at least one of the plurality of capping segments comprises:

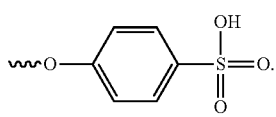

18. The structured organic film (SOF) membrane of claim 17, wherein at least one of the plurality of capping segments further comprises a sulfonic acid.

* * * * *